United States Patent [19]
Bonutti et al.

[11] Patent Number: 5,848,979
[45] Date of Patent: Dec. 15, 1998

[54] ORTHOSIS

[75] Inventors: Peter M. Bonutti; Boris P. Bonutti, both of Effingham, Ill.

[73] Assignee: Peter M. Bonutti, Effingham, Ill.

[21] Appl. No.: 683,196

[22] Filed: Jul. 18, 1996

[51] Int. Cl.⁶ .................. A61H 1/02; A61F 5/00
[52] U.S. Cl. .................. 601/5; 602/16; 602/20; 602/21; 601/33; 482/45
[58] Field of Search .................. 601/5, 27, 32, 601/33, 40, 34; 602/20, 21, 16, 5, 23; 482/45, 907

[56] References Cited

U.S. PATENT DOCUMENTS

| | | | |
|---|---|---|---|
| 2,206,902 | 7/1940 | Kost | 601/27 |
| 2,246,689 | 6/1941 | Kost | 601/33 |
| 2,832,334 | 4/1958 | Whitelaw . | |
| 4,538,595 | 9/1985 | Hajianpour . | |
| 4,576,151 | 3/1986 | Carmichael et al. | 602/24 |
| 4,716,889 | 1/1988 | Saringer | 601/33 |
| 5,100,403 | 3/1992 | Hotchkiss et al. | 601/33 |
| 5,102,411 | 4/1992 | Hotchkiss et al. | 601/33 |
| 5,203,321 | 4/1993 | Donovan et al. | 601/5 |
| 5,211,161 | 5/1993 | Stef | 601/5 |
| 5,285,773 | 2/1994 | Bonutti et al. | 602/16 |
| 5,349,956 | 9/1994 | Bonutti . | |
| 5,372,597 | 12/1994 | Hotchkiss et al. | 602/20 |
| 5,466,213 | 11/1995 | Hogan et al. | 601/33 |
| 5,503,619 | 4/1996 | Bonutti . | |

FOREIGN PATENT DOCUMENTS

| | | | |
|---|---|---|---|
| 2661333 | 10/1991 | France | 482/45 |
| 4261657 | 9/1992 | Japan | 601/33 |
| 1158195 | 5/1985 | U.S.S.R. | 601/33 |
| 1671296 | 8/1991 | U.S.S.R. | 601/33 |

Primary Examiner—Richard J. Apley
Assistant Examiner—Victor K. Hwang
Attorney, Agent, or Firm—Tarolli, Sundheim, Covell, Tummino & Szabo

[57] ABSTRACT

An orthosis is operable to vary the extent of supination or pronation of a hand connected with an arm of a patient. The orthosis includes a lower cuff which grips distal end portions of the ulna and radius in a lower portion of the arm of the patient. An upper cuff grips an upper portion of the arm of the patient. A drive assembly is operable to rotate the lower cuff and the distal end portions of the ulna and radius about an axis which extends through the wrist and elbow of the arm of the patient while the upper portion of the arm of the patient is held against movement by the upper cuff. The drive assembly includes a main gear which is connected with the lower cuff and a base of the orthosis. The lower cuff extends through a central opening in the main gear and is rotatable with the main gear about the axis which extends through the wrist and elbow of the patient. A second drive assembly may be provided to move sections of the base relative to each other to bend the elbow of the patient.

128 Claims, 7 Drawing Sheets

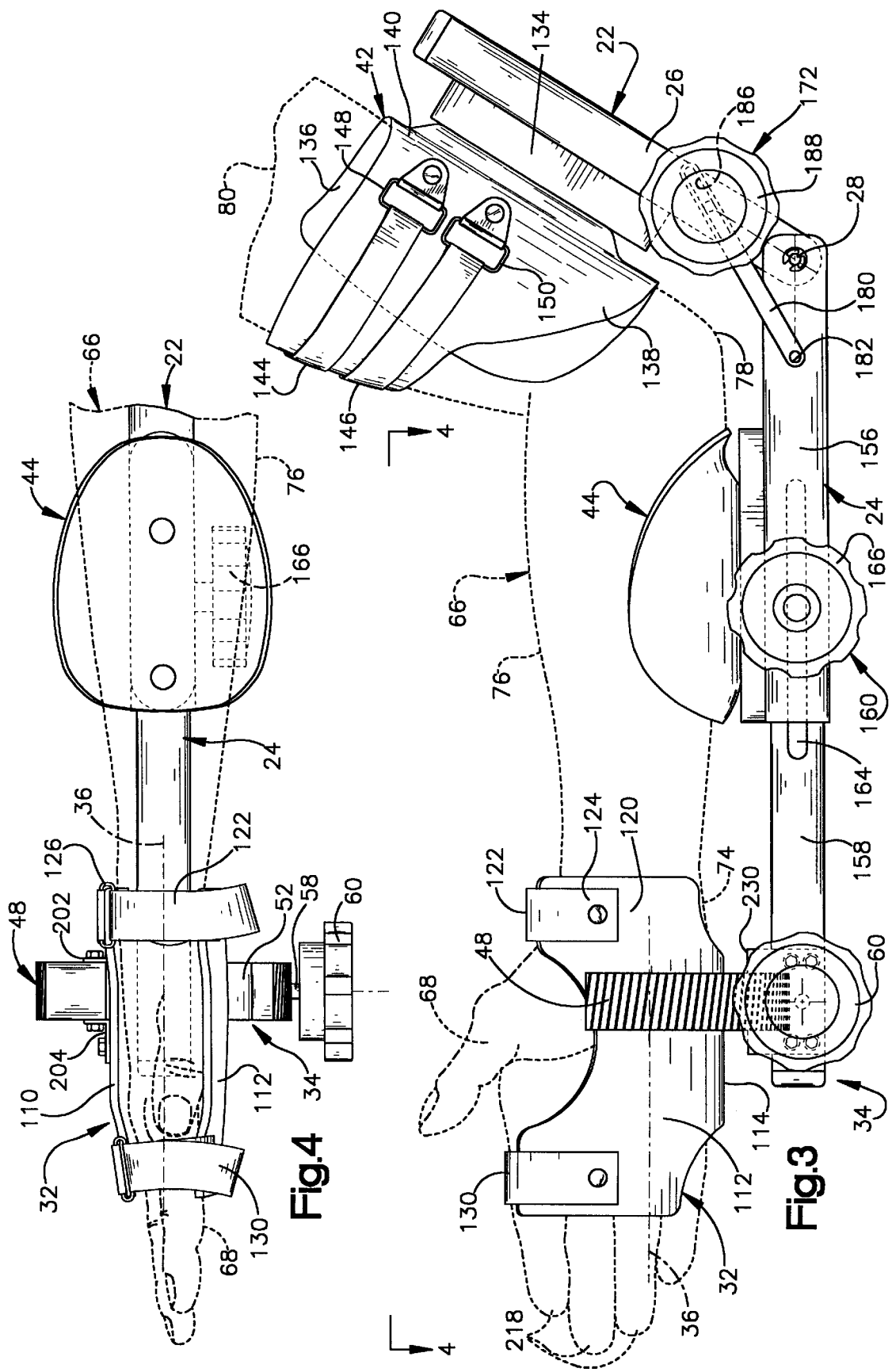

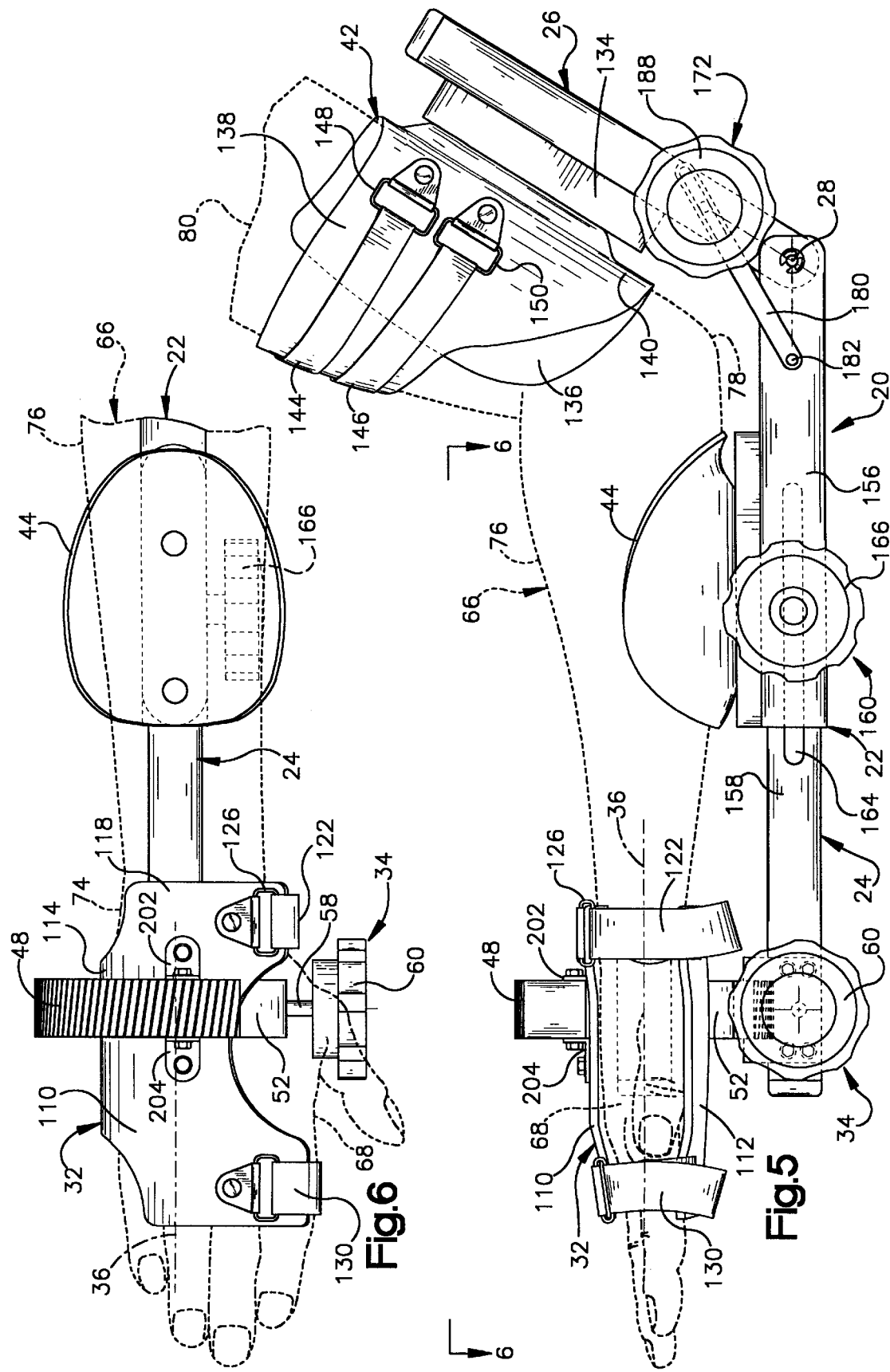

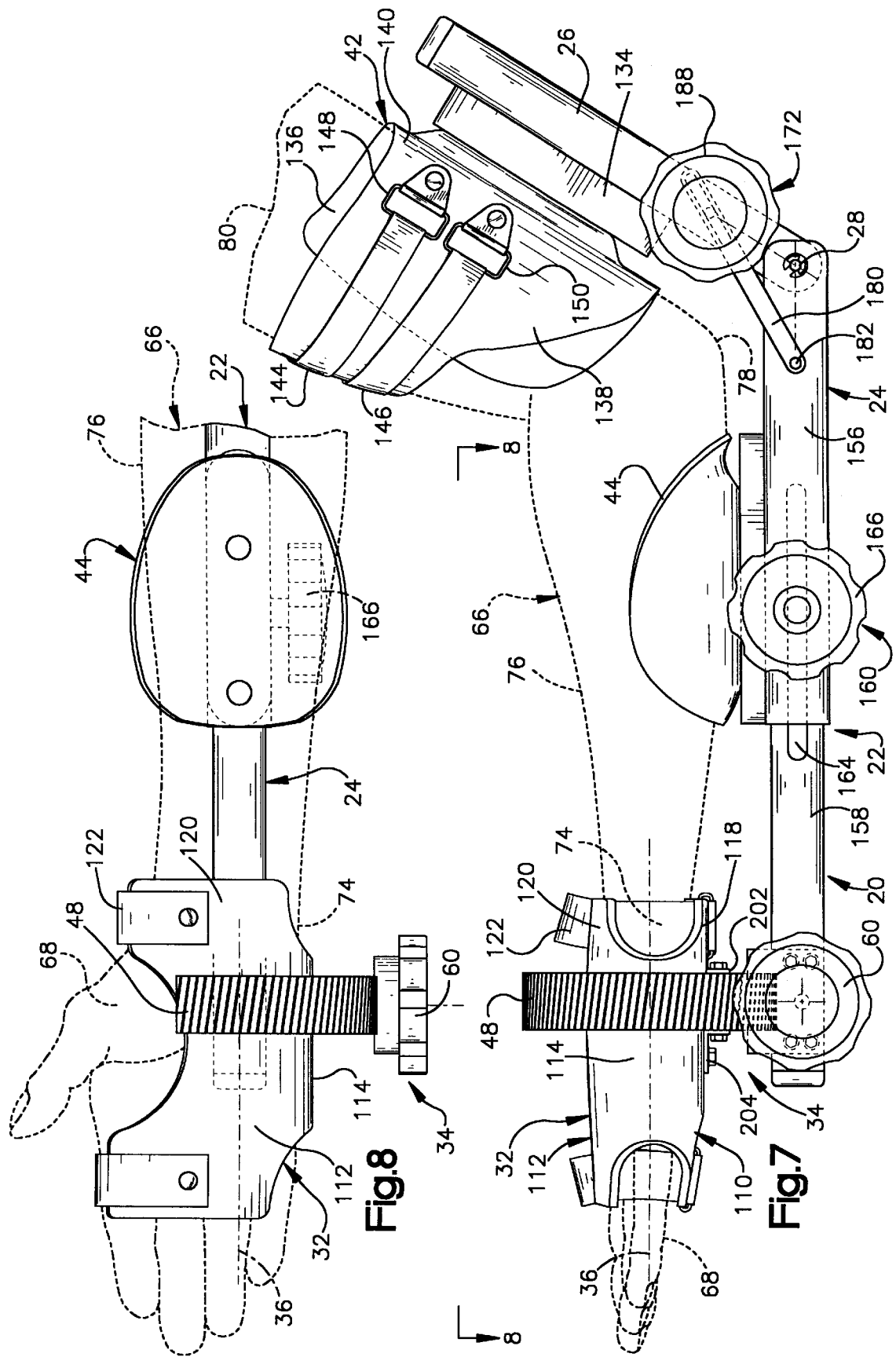

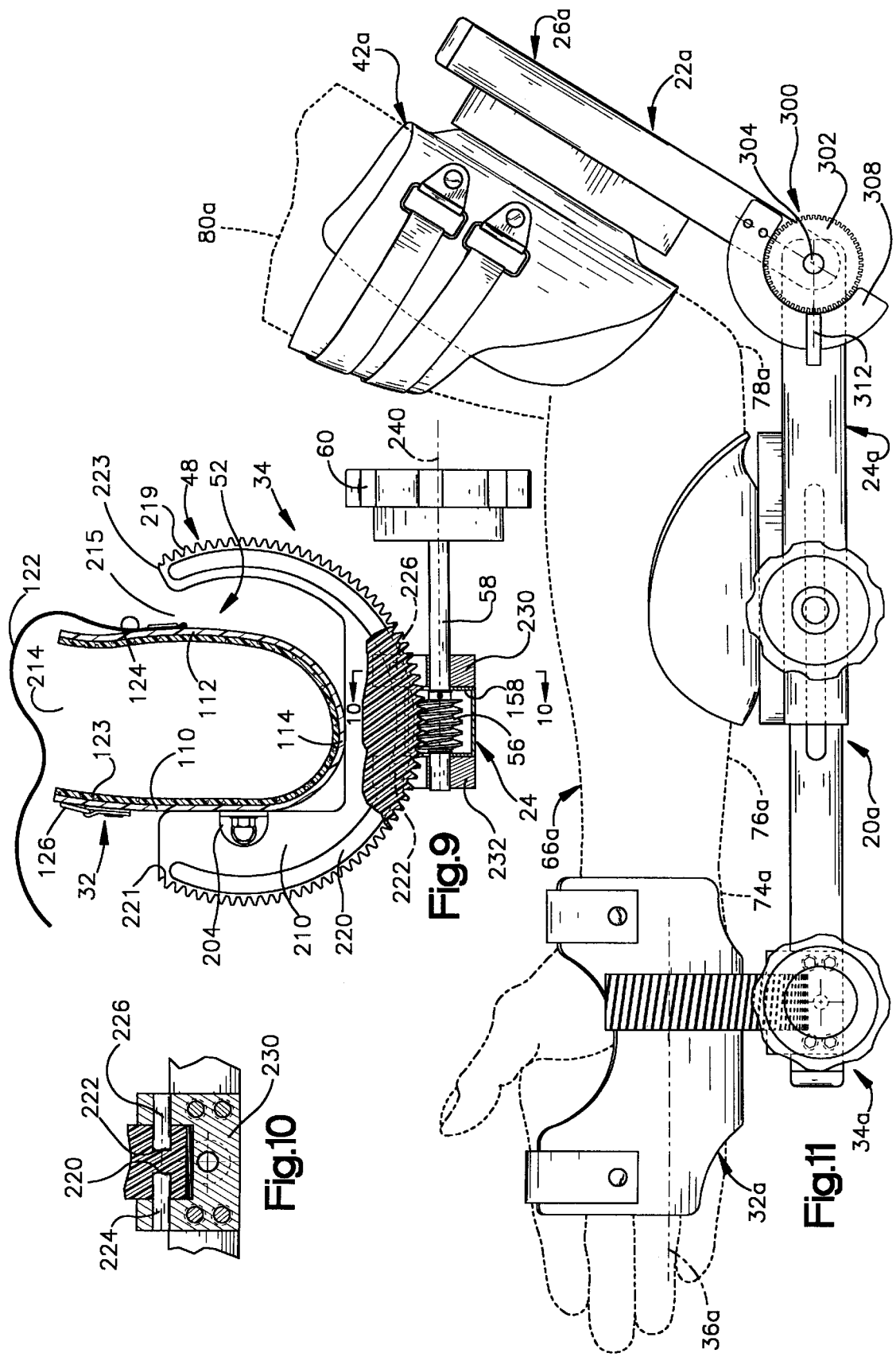

ABOUT THIS PAGE:

ORTHOSIS

BACKGROUND OF THE INVENTION

The present invention relates to a new and improved orthosis and method of using the orthosis to effect relative movement between bones in an arm or other portion of a body of a patient.

During supination or pronation of a hand of a patient, the ulna and radius bones in the lower portion of the arm of the patient move relative to each other. During treatment of a patient, it may be desirable to stretch viscoelastic body tissue connected with the ulna and radius bones and/or with the humerus in the arm of a patient in order to obtain a greater range of supination or pronation of the hand of the patient. In addition, it is contemplated that it may be desired to bend the elbow of the patient in either flexion or extension during treatment of the patient.

SUMMARY OF THE INVENTION

The present invention provides a new and improved apparatus and method for use in effecting relative movement between bones in an arm or other portion of a body of a patient. The apparatus includes an orthosis having a lower cuff which is rotatable relative to a base by a drive assembly and an upper cuff which is connected to the base. The lower cuff grips a wrist of the patient while the upper cuff grips the upper portion of an arm of the patient. The drive assembly rotates the lower cuff about an axis which extends along the lower portion of the arm.

The drive assembly for rotating the lower cuff may include a main gear which is connected with the lower cuff. The lower cuff may extend through an opening in the main gear. A drive gear connected with the base is disposed in engagement with the main gear and is rotatable relative to the base to rotate the main gear and lower cuff.

A second drive assembly may be provided to move sections of the base relative to each other and effect bending of the elbow in the arm of the patient. The second drive assembly is operable to pivot the sections of the base about an axis which extends transversely to the axis about which the lower cuff is rotated. Although it is believed that the apparatus and method of the invention will be particularly advantageous when used in association with an arm of a patient, they may be used in association with other portions of a patient's body.

BRIEF DESCRIPTION OF THE DRAWINGS

The foregoing and other features of the invention will become more apparent upon a consideration of the following description taken in connection with the accompanying drawings, wherein:

FIG. 3 is a side elevational view illustrating the manner in which the arm of the patient is gripped by upper and lower cuffs of the orthosis of FIG. 1;

FIG. 4 is a plan view, taken generally along the line 4—4 of FIG. 3, further illustrating the relationship of the lower cuff of the orthosis to a wrist and hand of the patient;

FIG. 5 is a side elevational view, generally similar to FIG. 3, illustrating the manner in which the orthosis effects pronation of the hand of the patient;

FIG. 6 is a plan view, taken generally along the line 6—6 of FIG. 5 further illustrating the relationship of the lower cuff of the orthosis to the wrist and hand of the patient;

FIG. 7 is a side elevational view, generally similar to FIG. 3, illustrating the manner in which the orthosis effects supination of the hand of the patient;

FIG. 8 is a plan view, taken generally along the line 8—8 of FIG. 7, further illustrating the relationship of the lower cuff of the orthosis to the wrist and hand of the patient;

FIG. 9 is a fragmentary sectional view, taken generally along the line 9—9 of FIG. 1, illustrating the relationship of the lower cuff to a drive assembly which rotates the lower cuff;

FIG. 10 is a fragmentary sectional view, taken generally along the line 10—10 of FIG. 9, illustrating the manner in which a pair of pins engage a track in a main gear in the drive assembly to rotatably support the main gear;

FIG. 11 is a side elevational view, generally similar to FIG. 3, of a second embodiment of the orthosis.

DESCRIPTION OF SPECIFIC PREFERRED EMBODIMENTS OF THE INVENTION

General Description

Figure 1:
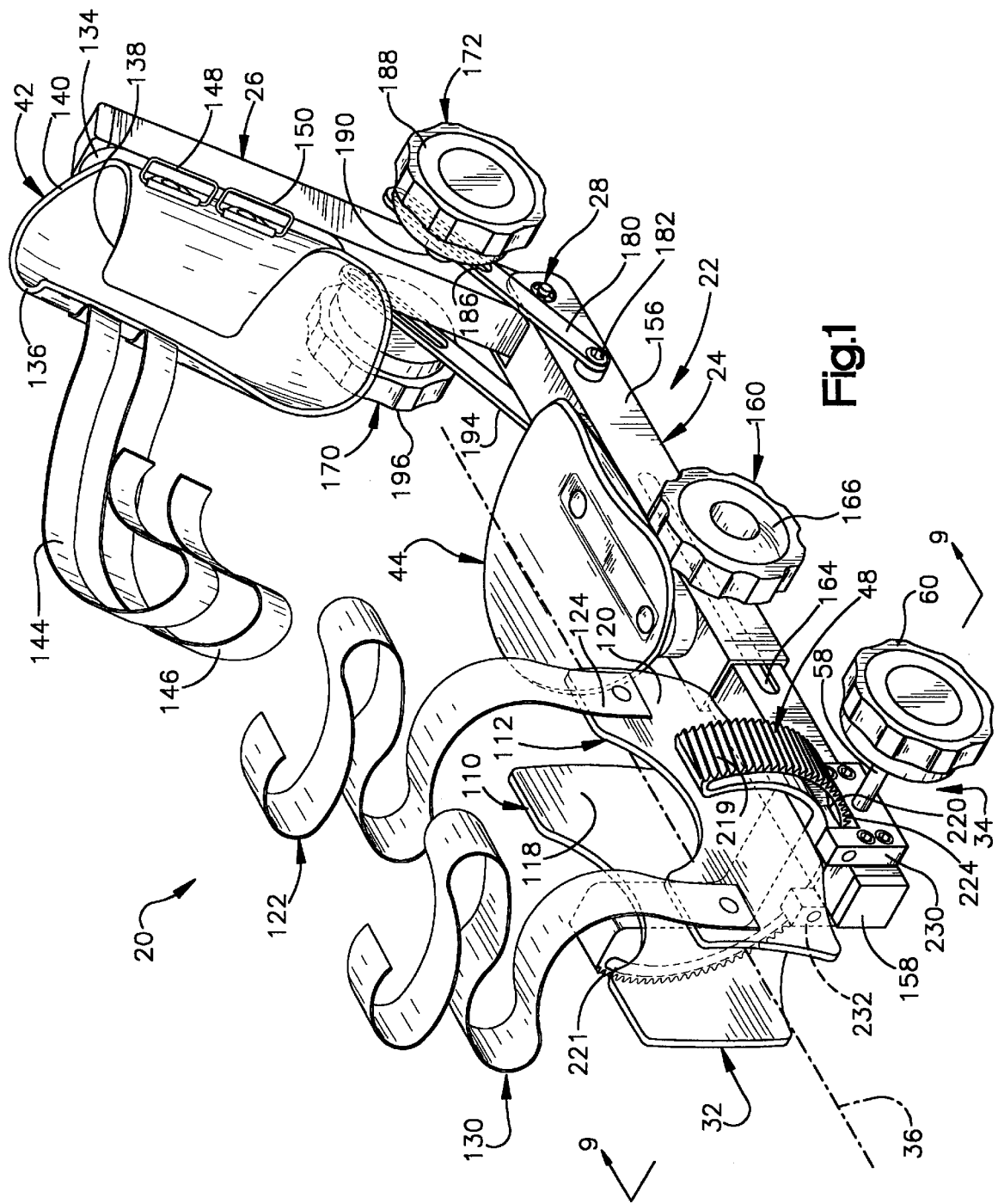
FIG. 1 is a pictorial illustration of an orthosis which is constructed and used in accordance with the present invention.

An orthosis 20 for effecting relative movement between bones in an arm of a patient is illustrated in FIG. 1. Although it is preferred to use the orthosis 20 to effect relative movement between bones in an arm of a patient, it is contemplated that an orthosis constructed in accordance with the present invention could be utilized to effect movement between bones in other portions of a patient's body. Of course, the size and/or the relationship of various components of the orthosis 20 may be modified to adapt the orthosis for use with other portions of a patient's body.

The orthosis 20 includes a base 22. The base 22 includes a lower cuff arm 24 which is adapted to extend along a lower portion of an arm of a patient. The base 22 also includes an upper cuff arm 26 which is adapted to extend along an upper portion of an arm of a patient. The lower cuff arm 24 and upper cuff arm 26 are interconnected at a pivot connection 28.

A first or lower cuff 32 is connected with the lower cuff arm 24 by a main drive assembly 34. The lower cuff 32 grips the wrist and hand of a patient. If desired, the lower cuff 32 could be constructed so as to grip only the wrist of the patient.

In accordance with a feature of the invention, the main drive assembly 34 is operable to rotate the lower cuff 32 and the gripped portion of the wrist and hand of the patient about an axis 36. The axis 36 extends parallel to a longitudinal central axis of the lower cuff arm 24. When an arm of a patient is held by the orthosis 20, the axis 36 extends along the lower portion of the arm of the patient through the wrist and elbow. Rotation of the lower cuff 32 about the axis 36 by the main drive assembly 34 varies the extent of pronation and/or supination of the hand of the patient.

A second or upper cuff 42 is fixedly connected with the upper cuff arm 26. The upper cuff 42 grips the upper portion of the arm of the patient. The upper cuff 42 holds the upper portion of the arm of the patient against movement relative to the upper cuff arm 26 and lower cuff arm 24 during rotation of the lower cuff 32 about the axis 36.

Since the upper portion of the patient's arm is held by the upper cuff 42, rotational movement of the hand and wrist of the patient by the lower cuff 32 during operation of the main drive assembly 34 effects relative movement between bones in the lower portion of the arm of the patient without moving bones in the upper portion of the arm of the patient. Thus, the upper cuff 26 and base 22 cooperate to isolate movement to the lower portion of the patient's arm. Therefore, rotation of the lower cuff 32 about the axis 36 causes movement of only bones in the lower portion of the arm of the patient.

A third or center cuff 44 is disposed on the lower cuff arm 24 and is engageable with the lower portion of the arm of the patient. The center cuff 44 is ineffective to restrain movement of bones in the lower portion of the arm of the patient. The center cuff 44 merely provides a support for the lower arm of the patient to increase the patient's comfort during use of the orthosis 20.

The main drive assembly 34 includes a main gear 48 which is connected with the lower cuff arm 24. The main gear 48 and lower cuff 32 have central axes which are coincident with the axis 36. The main gear 48 and lower cuff 32 are rotated together about the axis 36 during operation of the drive assembly 34.

In the illustrated embodiment of the invention, the lower cuff 32 extends through a central opening 52 (FIG. 9) in the main gear 48. However, if desired, the main gear 48 could be connected with one end portion of the lower cuff 32 so that the lower cuff does not extend through the main gear. It is believed that it will be preferred to have the lower cuff 32 extend through the main gear 48 in order to provide a solid interconnection between the lower cuff 32 and the main gear and to promote the stability of the lower cuff relative to the main drive assembly 34.

The main drive assembly 34 includes a worm or drive gear 56 (FIG. 9) which is disposed in meshing engagement with the main gear 48. The drive gear or worm 56 is rotatably mounted on the lower cuff arm 24 and is fixedly connected with a shaft 58. A knob 60 on an outer end portion of the shaft 58 is manually rotatable to rotate the drive gear 56 and main gear 48. As this occurs, the main gear 48 and lower cuff 32 are rotated about the axis 36 (FIG. 1). It is contemplated that the main drive assembly 34 could have a different construction if desired.

Patient's Arm

Figure 2:
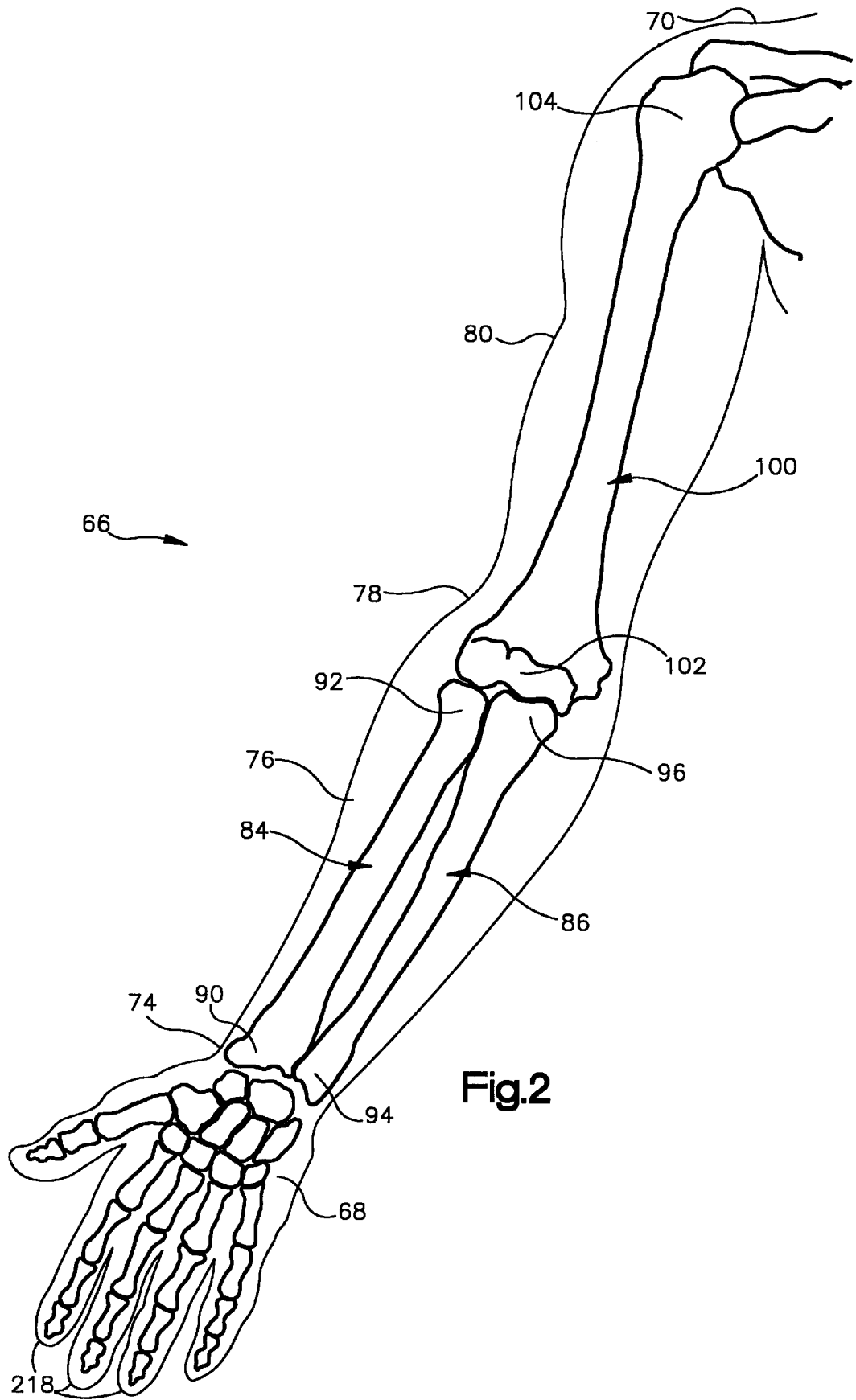
FIG. 2 is an illustration of a right anterior arm of a patient.

Although the orthosis 20 could be utilized with either the right or left arm of a patient, a right arm 66 of the patient is illustrated in FIG. 2. The arm 66 of the patient extends between a hand 68 and shoulder 70 of the patient. The right arm 66 of the patient includes a wrist 74, a lower portion or forearm 76, an elbow 78, and an upper portion 80. The wrist 74 is the region where the hand 68 is joined with the lower portion 76 of the arm 66 of the patient. The elbow 78 is the region where the lower portion 76 of the arm 66 and the upper portion 80 of the arm are joined.

The lower portion 76 of the arm 66 includes a radius bone 84 and an ulna bone 86. The radius 84 has a distal end portion or capitulum 90 at the wrist 74. The radius has a proximal end portion or capitulum 92 at the elbow 78. Similarly, the ulna 86 has a distal end portion or capitulum 94 at the wrist 74. The ulna 86 has a proximal end portion or capitulum 96 at the elbow 78.

The upper portion 80 of the arm 66 extends between the shoulder 70 and elbow 78. The upper portion 80 of the arm includes the humerus bone 100. The humerus 100 has a distal end portion or capitulum 102 which cooperates with the proximal end portions 92 and 96 of the radius 84 and ulna 86. In addition, the humerus 100 has a proximal end portion 104 which cooperates with the shoulder 70.

Pronation of the hand 68 occurs when the hand is turned so that the palmar or anterior side of the hand and wrist 74 face downward and the opposite or posterior side of the hand and wrist face upward. Supination of the hand 68 occurs when the hand is turned so that the palmar or anterior side of the hand and wrist 74 face upward and the opposite or posterior side of the hand and wrist face downward. During supination and pronation of the hand 68, the radius and ulna 84 and 86 move relative to each other. The orthosis 20 grips the wrist 74 and upper portion 80 of the arm 66 of the patient to isolate movement to the radius 84 and ulna 86 during pronation and/or supination of the hand.

Although the foregoing explanation has been in conjunction with the right arm 66 of a patient, it should be understood that the orthosis 20 could be used with the left arm of a patient. It should also be understood that the orthosis 20 may be used with a portion of a patient's body other than an arm. The orthosis 20 is designed to isolate relative movement of a portion of a body disposed on one side of a joint from a portion of a body disposed on the other side of the joint. Thus, in the case of the arm 66, the orthosis 20 isolates rotational movement of the distal end portions 90 and 94 of the radius and ulna 84 and 86 from the upper portion 80 of the arm 66.

Cuffs

The lower cuff 32 firmly grips and transmits force from the main drive assembly 34 to the wrist 74 of a patient (FIGS. 3 and 4). The lower cuff 32 includes a pair of generally parallel sidewalls 110 and 112 (FIGS. 1, 3, 4, and 9). The sidewalls 110 and 112 are integrally formed as one piece of a polymeric material having sufficient rigidity to be self-supporting and to apply force against the wrist 74 (FIG. 3) of the arm 66. However, the sidewalls 110 and 112 have sufficient flexibility to enable them to be flexed to a limited extent and pressed firmly against the wrist 74.

In addition to gripping the wrist 74, the sidewalls 110 and 112 of the lower cuff 32 grip the hand 68 connected with the arm 66. An arcuate connector wall 114 (FIG. 9) extends between and is integrally formed as one piece with the sidewalls 110 and 112. The connector wall 114 is sufficiently flexible to enable the connector wall to deflect to accommodate hands 68 of different sizes. If desired, the axial extent of the side walls 110 and 112 could be reduced so that they would be effective to grip only the wrist 74.

The axis 36 (FIG. 3), about which the lower cuff 32 and main gear 48 rotate, extends midway between the sidewalls 110 and 112 (FIG. 4). The axis 36 is offset upward (as viewed in FIG. 3) from the center of curvature of the connector wall 114 (FIG. 3). The axis 36 extends parallel to a longitudinal central axis of the connector wall 114. In addition, the axis 36 extends parallel to a longitudinal central axis of the lower cuff arm 24 and extends through the wrist 74 and elbow 78.

The sidewalls 110 and 112 of the lower cuff 32 include a pair of sections 118 and 120 which securely grip the wrist portion 74 of the arm 66 (FIGS. 1, 3, 6, 7 and 8). The sections 118 and 120 of the sidewalls 110 and 112 are firmly pressed against opposite sides of the wrist 74 by a wrist strap 122. The wrist strap 122 presses a resilient foam lining 123 (FIG. 9) on the inner side of the lower cuff 32 firmly against the wrist 74.

The distal end portions or capitula 90 and 94 of the radius and ulna 84 and 86 (FIG. 2) are firmly gripped between the opposite sections 118 and 120 (FIG. 1) of the sidewalls 110 and 112 of the lower cuff 32. This results in the distal end portions 90 and 94 of the radius and ulna 84 and 86 being held against movement, in directions perpendicular to the axis 36, by the sections 118 and 120 of the sidewalls 110 and 112 of the lower cuff 32 during rotation of the lower cuff 32 about the axis 36. However, the distal end portions 90 and 94 of the radius and ulna 84 and 86 can rotate somewhat about their central axes during rotation of the lower cuff 32 about the axis 36.

In the illustrated embodiment of the lower cuff 32, the wrist strap 122 has an end portion 124 (FIG. 3) which is fixedly connected to the section 120 of the sidewall 112 of the lower cuff 32. The wrist strap 122 extends through a ring 126 (FIG. 6) mounted on the section 118 of the opposite sidewall 110. The wrist strap 122 is formed with sections of hook and loop fastener material, i.e.,"VELCRO" (trademark). The strap section of loop fastener material can be pressed against the strap section of hook fastener material to interconnect the sections of the wrist strap 122.

The wrist strap 122 transmits force between the sections 118 and 120 of the sidewalls 110 and 112 of the lower cuff 32. This force presses the sections 118 and 120 of the sidewalls 110 and 112 of the lower cuff 32 firmly against the wrist 74 to grip the distal end portions 90 and 94 of the radius and ulna 84 and 86. Of course, a different type of cuff with a different type of strap or other type of interconnection could be utilized if desired, as long as the lower cuff 32 is firmly pressed against the wrist 74. For example, the sections 118 and 120 of the side walls 110 and 112 of the lower cuff 32 could completely enclose the wrist 74 and could have overlapping portions connected to each other.

A second or hand strap 130 is connected with the sidewalls 110 and 112 of the lower cuff 32 in the same manner as in which the wrist strap 122 is connected with the sidewalls 110 and 112 of the lower cuff 32. The hand strap 130 presses the sidewalls 110 and 112 of the lower cuff firmly against the palmar side and back side of the hand 68 (FIGS. 3 and 4) to firmly grip the hand. Thus, both the hand 68 and wrist 74 are firmly gripped by the lower cuff 32. However, the portion of the lower cuff 32 which grips the wrist 74 is particularly important since it also grips the distal end portions 90 and 94 of the radius and ulna bones 84 and 86.

The upper cuff 42 (FIGS. 1 and 3) has the same general construction as the lower cuff 32. The upper cuff 42 grips the upper portion 80 of the arm 66 and holds the upper portion 80 of the arm 66 against movement relative to the lower portion 76 of the arm 66 during rotation of the cuff 32 about the axis 36. The upper cuff 42 is fixedly connected to the upper cuff arm 26 of the base 22 by a connector block 134.

The upper cuff 42 includes a pair of sidewalls 136 and 138. The sidewalls 136 and 138 (FIG. 1) are integrally formed as one piece of a polymeric material having sufficient rigidity to be self-supporting while still enabling the material to be flexed to a limited extent. The sidewalls 136 and 138 of the upper cuff 42 are formed of the same material as the sidewalls 110 and 112 of the lower cuff 32.

A central axis of the upper cuff 42 is disposed midway between the sidewalls 136 and 138 and extends parallel to the longitudinal central axis of the upper cuff arm 26. The central axis of the upper cuff 42 intersects the axis 36 about which the lower cuff 32 is rotated by operation of the main drive assembly 34.

An arcuate connector section 140 extends between the sidewalls 136 and 138 of the upper cuff 42. The connector section 140 of the upper cuff is fixedly connected to the upper cuff arm 26 by the connector block 134. A pair of straps 144 and 146 are connected with the sidewall 136 of the upper cuff 42 and are engageable with rings 148 and 150 connected with the sidewall 138 of the upper cuff 42. The straps 144 and 146 extend through the rings 148 and 150 and press the two sidewalls 136 and 138 of the upper cuff 42 firmly against the upper portion 80 of a patient's arm.

The straps 144 and 146 have sections formed of hook and loop fastener material, i.e., "VELCRO" (trademark). The hook and loop fastener sections in each of the straps 144 and 146 connect sections of the straps together. The straps 144 and 146 interconnect the two sidewalls 136 and 138 and press them together. Of course, the upper cuff 42 and/or straps 144 and 146 could have a different construction if desired, so long as the upper cuff firmly holds the upper portion 80 of the arm of a patient against movement relative to the lower portion 76 of the arm during rotation of the lower cuff 32 about the axis 36.

In the illustrated embodiment of the orthosis 20, the upper cuff 42 is fixedly connected to the upper cuff arm 26 through the connector block 134. If desired, the upper cuff 42 could be mounted for axial movement along the upper cuff arm 26. If this was done, a suitable fastener arrangement would be provided to lock the upper cuff 42 in any desired position along the upper cuff arm 26.

A third or center cuff 44 (FIGS. 3 and 4) is provided to support the lower portion 76 of the arm 66 of the patient. The center cuff 44 is formed of the same polymeric material as the lower cuff 32 and upper cuff 42. The center cuff 44 increases the comfort of the patient by providing a resting location for the lower portion 76 of the patient's arm 66. The center cuff 44 does not restrain the lower portion 76 of the patient's arm 66. There are no straps associated with the center cuff 44. Therefore, the lower portion 76 of the patient's arm 66 is free to move relative to the upper portion 80 of the patient's arm when the lower cuff 32 is rotated about the axis 36 by the main drive assembly 34.

Base

The base 22 (FIGS. 1 and 3) of the orthosis 20 supports the lower cuff 32 and upper cuff 42. During operation of the main drive assembly 34 to rotate the lower cuff 32 relative to the upper cuff 42, force is transmitted through the base 22 to retain the upper cuff against movement. In addition, the base 22 supports the lower cuff 32 and main drive assembly 34 in such a manner as to enable the lower cuff to be rotated relative to the base.

The base 20 includes the lower and upper cuff arms 24 and 26. The longitudinally extending lower cuff arm 24 includes a base section 156 and an extension section 158. The extension section 158 is telescopically received in the base section 156. The center cuff 44 is fixedly connected to the base section 156 of the lower cuff arm 24.

Upon operation of a retainer assembly 160 to a disengaged condition, the extension section 158 can be moved axially into and out of the base section 156 to vary the length of the lower cuff arm 24. Thus, the extension section 158 is moved axially into the base section 156 to decrease the length of the lower cuff arm 24. The extension section is pulled axially out of the base section to increase the length of the lower cuff arm 24. This enables the orthosis 20 to accommodate patients having arms 66 with lower portions 76 of different lengths.

The retainer assembly 160 includes a bolt (not shown) having a head end portion disposed within the extension section 158 and a shank portion which extends through a slot 164 (FIG. 3) in the extension section 158. The shank portion of the bolt also extends through a hole (not shown) in the base section 156 of the lower cuff arm 24. A knob 166 is threaded onto the shank portion of the bolt.

Upon manual tightening of the knob 166, the head end portion of the bolt firmly presses the extension section 158 against the base section 156 of the lower cuff arm 24. This locks the base and extension sections 156 and 158 against axial movement relative to each other. Upon rotation of the knob 166 to loosen the bolt, the extension section 158 can be moved relative to the base section 156 to either increase or decrease the axial extent of the lower cuff arm 24.

The base section 156 and extension section 158 of the lower cuff arm 24 both have rectangular cross-sectional configurations. The rectangular cross-sectional configurations of the base section 156 and extension section 158 prevents rotational movement between the base and extension sections about their coincident longitudinal central axes. The coincident longitudinal central axes of the base section 156 and extension section 158 of the lower cuff arm 24 extend parallel to the axis 36 about which the main drive assembly 24 rotates the lower cuff 32.

The upper cuff arm 26 is pivotally connected with the base section 156 of the lower cuff arm 24 at the pivot connection 28. A pair of identical retainer assemblies 170 and 172 (FIG. 1) are operable between an engaged condition and a release condition. When the retainer assemblies 170 and 172 are in the engaged condition, they hold the lower and upper cuff arms 24 and 26 against movement relative to each other about the pivot connection 28. When the retainer assemblies 170 and 172 are in the disengaged condition they enable the lower cuff arm 24 to pivot relative to the upper cuff arm 26 at the pivot connection 28 about an axis which extends perpendicular to the axis 36.

When the retainer assemblies 170 and 172 are in a disengaged condition, the upper cuff arm 26 is pivotal in a clockwise direction (as viewed in FIG. 1) about the pivot connection 28. This enables the upper cuff arm 26 to move to a position in which the longitudinal central axis of the upper cuff arm 26 is coincident with the longitudinal central axis of the lower cuff arm 24. When the lower cuff arm 24 and upper cuff arm 26 are in this relationship relative to each other, the base 22 has a straight linear configuration.

The upper cuff arm is pivotal in a counterclockwise direction from the orientation in which the base 22 has a straight linear configuration, through a range of approximately 90° about the pivot connection 28. The retainer assemblies 170 and 172 are operable from the disengaged condition to the engaged condition to lock the upper cuff arm 26 in any desired angular orientation relative to the lower cuff arm 24. Thus, when the retainer assemblies 170 and 172 are in the disengaged condition, the upper cuff arm 26 is movable between a position in which its longitudinal axis extend perpendicular to and intersects a longitudinal central axis of the lower cuff arm 24 to a position in which the longitudinal central axis of the upper cuff arm 26 is coincident with the longitudinal central axis of the lower cuff arm 24. The retainer assemblies 170 and 172 may be engaged when the upper cuff arm 26 is at any position between the two limit positions to hold the upper cuff arm 26 against pivotal movement relative to the lower cuff arm 24.

The retainer assembly 172 (FIGS. 1 and 3) includes a connector link 180 having an end portion which is pivotally connected at 182 with the base section 156 of the lower cuff arm 24. The connector link 180 has a longitudinally extending slot 186 at the end of the connector link opposite from the pivot connection 182. A shank portion of a bolt (not shown) in the retainer assembly 172 extends through the slot 186 and into a manually rotatable knob 188. A head end portion of the bolt is disposed within the upper cuff arm 26.

Upon rotation of the knob 188 in a clockwise direction (as viewed in FIG. 1) the retainer assembly 172 is operated from the disengaged condition to the engaged condition. As this occurs, the connector link 180 is firmly clamped between spacers 190 on the shank portion of the bolt and the knob 188 to lock the upper cuff arm 26 against movement relative to the lower cuff arm 24. Upon rotation of the knob 188 in a counterclockwise direction (as viewed in FIG. 1) the connector link 180 is released and the upper cuff arm 26 is pivotal relative to the lower cuff arm 24 about the pivot connection 28.

The retainer assembly 170 has the same construction as the retainer assembly 172. Thus, the retainer 170 includes a connector link 194 and a knob 196 (FIG. 1). The knob 196 in the retainer assembly 170 is rotatable to an engaged condition in which the connector link 194 is firmly gripped and a release condition in which the connector link is movable relative to the knob 196.

In the illustrated embodiment of the invention, the lower cuff arm 24 and the upper cuff arm 26 are movable relative to each other about the pivot connection 28. If desired, the lower cuff arm 24 could be fixedly connected with the upper cuff arm 26. If this was done, the upper cuff arm 26 could be formed as one piece with the base section 156 of the lower cuff arm 24. The upper cuff arm 26 and base section 156 of the lower cuff arm 24 could be disposed in a linear orientation or in an angular orientation, as shown in FIG. 1. It is believed that it will be preferred to construct the orthosis 20 in such a manner as to enable the lower cuff arm 24 and upper cuff arm 26 to move relative to each other to accommodate different orientations of the upper portion 80 (FIG. 3) of the arm 66 of a patient relative to the lower portion 76 of the arm.

Main Drive Assembly

The main drive assembly 34 (FIG. 3) rotates the lower cuff 32 about the axis 36 which extends through the wrist 74 and elbow 78 of the arm 66 of the patient. The axis 36 extends generally parallel to and is at least reasonably close to being coincident with the longitudinal central axis of the lower portion 76 of the arm 66. The axis 36 extends along the radius and ulna 84 and 86 (FIG. 2).

Although axis 36 is generally parallel to central axes of the radius and ulna 84 and 86, the axis 36 is offset from the central axes of the radius and ulna. A portion of the axis 36 may extend through space between the radius 84 and ulna 86. It is contemplated that the precise location of the radius and ulna 84 and 86 relative to the axis 36 will vary from patient to patient.

The main drive assembly 34 is connected with the lower cuff arm 24 and is operable to rotate the lower cuff 32 about the axis 36. The lower cuff 32 extends through the central opening 52 (FIG. 9) in the main gear 48. The sidewall 110 of the lower cuff is fixedly connected with the main gear 48 by a pair of right angle brackets 202 and 204 (FIGS. 5 and 6). The brackets 202 and 204 connect the sidewall 110 of the lower cuff 32 to a wall 210 (FIG. 9) of the main gear 48. If desired, the main gear 48 could be integrally formed as one piece with the lower cuff 32.

The brackets 202 and 204 connect the lower cuff 32 to the main gear 48 with an entry opening 214 (FIG. 9) to the lower cuff facing in the same direction, that is upward as viewed in FIG. 9, as the generally U-shaped central opening 52 in the main gear 48. Thus, the central opening 52 in the main gear 48 has an open upper (as viewed in FIG. 9) portion 215 through which the side walls 110 and 112 of the lower cuff 32 extend. The side walls 110 and 112 of the lower cuff 32 define the entry opening 214 to the lower cuff. The entry opening 214 to the lower cuff 32 is vertically aligned (as viewed in FIG. 9) with the open upper portion 215 of the opening through the main gear 48.

When the wrist strap 122 and hand strap 130 are in the disconnected condition of FIG. 1, the patient's hand 68 can be moved downward through the opening 214 (FIG. 9) into the lower cuff 32 and into the central opening 52 in the main gear 48. When this has been done, the wrist 74 of the patient will be disposed on one side, i.e., the right side as viewed in FIG. 3, of the main gear 48 while ends of fingers 218 will be disposed on the opposite side, i.e., the left side, as viewed in FIG. 3, of the main gear 48. The palmar portion of the hand 68 of the patient will be disposed in the lower cuff 32 and in the central opening 52 in the main gear 48. The axis 36 will extend through the hand 68, wrist 74, and the lower portion 76 of the arm 66 of the patient.

If desired, the lower cuff 32 could be connected with the main gear 48 in a different manner. For example, the lower cuff 32 may only have a portion which grips the wrist 74 in the arm 66 of the patient and does not have a portion which grips the hand 68 of the patient. This construction would result in the portion of the lower cuff 32 disposed to the left (as viewed in FIG. 3) of the main gear 48 being omitted. Alternatively, the lower cuff arm 24 could be extended so that the main drive assembly 34 is disposed to the left (as viewed in FIG. 3) of the fingers 218 on the hand 68 of the patient. The lower cuff 32 would then extend past the ends of the fingers 218 on the hand of the patient and be connected to the main gear 48.

The main gear 48 includes an arcuate array 219 (FIG. 9) of gear teeth having a configuration of a portion of a circle. The cuff 32 extends upward (as viewed in FIG. 9) between opposite ends 221 and 223 of the arcuate array 219 of gear teeth and through the open upper portion of the U-shaped central opening 52 in the main gear 50. The arcuate array 219 of gear teeth has a central axis which is coincident with the axis 36 (FIG. 1) about which the main gear 48 rotates. If desired, the arcuate array 219 (FIG. 9) of gear teeth could be integrally formed as one piece with the side walls 110 and 112 and connector wall 114 of the lower cuff 32.

The main gear 48 is supported for rotation about the axis 36 by the lower cuff arm 24. The main gear 48 has a pair of identical tracks or grooves 220 and 222 (FIG. 10) disposed on opposite sides of the gear. The grooves 220 and 222 form portions of circles and have centers of curvature which are disposed on the axis 36.

A pair of pins engages each of the grooves 220 and 222. Thus, as shown in FIG. 10, a cylindrical pin 224 extends into the groove 220 and a cylindrical pin 226 extends into the groove 222. The pins 224 and 226 are supported in a coaxial relationship on the right (as viewed in FIG. 9) side of the lower cuff arm 24 by a mounting block 230. A second mounting block 232 is disposed adjacent to the left side of the lower cuff arm 24 and supports a second pair of pins which engage the tracks 220, 222 in the same manner in which the pins 224 and 226 engage the tracks. Therefore, a pair of pins extends into each of the tracks 220 and 222 to support the main gear 48 for rotation relative to the lower cuff arm 24.

It should be understood that a different mounting arrangement could be utilized for supporting the main gear 48. Thus, rather than having the tracks 220 and 222, a pair of arcuate ribs could extend from opposite sides of the wall 210 of the main gear 48. These ribs would extend into arcuate tracks which are fixedly connected with the lower cuff arm 24 and have a common central axis which is coincident with the axis 36. By having the support for the main gear 48 offset from the axis 36, it is possible to have the lower cuff 32 and/or the hand 68 of the patient extend through an opening 52 in the central portion of the main gear 48.

The drive gear 56 (FIG. 9) is fixedly connected with the shaft 58 and is disposed on meshing engagement with the arcuate array 219 of teeth on the main gear 48. In the illustrated embodiment of the main drive assembly 34, the drive gear 56 is a worm. Upon rotation of the knob 60, the worm 56 is rotated about an axis 240 which extends perpendicular to and is offset from the axis 36 (FIG. 1). If desired, a spur gear could be substituted for the drive gear 56. In addition, if desired, a suitable motor could be provided in place of the manually rotatable knob 60 to rotate the drive gear 56.

Use of Orthosis

Viscoelastic body tissue connecting the proximal end portions 92 and 96 (FIG. 2) of the radius and ulna 84 and 86 with the humerus 100 in the arm 66 of a patient may require stretching to enable the hand 68 of the patient to move through a desired range of motion in supination and/or pronation. When the viscoelastic body tissue connected with the proximal end portions 92 and 96 of the radius and ulna 84 and 86 is to be stretched, the upper portion 80 of the arm 66 of the patient is positioned in the upper cuff 42 (FIG. 1) of the orthosis 20. The straps 144 and 146 are loosely tightened around the upper portion 80 of the arm 66 to initially position the upper cuff arm 26 relative to the upper portion 80 of the patient's arm 66.

The retainer assemblies 170 and 172 (FIG. 1) are then loosened and the lower cuff arm 24 is positioned relative to the lower portion 76 of the patient's arm 66 (FIG. 2). At this time, the retainer 160 (FIG. 3) is loose. The extension section 158 of the lower cuff arm 24 is moved to position the lower cuff 32 relative to the hand 68 (FIG. 3). The retainer assemblies 170, 172 are tightened to fixedly interconnect the lower cuff arm 24 and upper cuff arm 26. The retainer assembly 160 is also tightened to hold the extension section 158 against movement relative to the base section 156 of the lower cuff arm 24. The upper cuff straps 144 and 146 are tightened to firmly grip the upper portion 80 of the patient's arm.

The hand 68 is positioned in the lower cuff 32 by moving the hand through the opening 214 (FIG. 9) in the lower cuff 32. The wrist strip 122 and hand strap 130 are then tightened. This presses the sidewalls 110 and 112 of the lower cuff 32 against the palmar and back sides of the wrist 74 and hand 68.

Once this has been done, the distal end portions 90 and 94 of the radius and ulna 84 and 86 are firmly gripped between the sidewalls 110 and 112 of the lower cuff 32. In addition, the hand 68 is firmly gripped between the sidewalls 110 and 112 of the lower cuff. The upper cuff 42 firmly grips the upper portion 80 of the patient's arm 66.

Until the main drive assembly 34 is actuated, the lower portion 76 and the upper portion 80 of the patient's arm 66 are held against movement relative to each other. Thus, the lower portion 76 of the arm 66 (FIG. 3) is held against movement relative to the lower cuff arm 24 by the lower cuff 32. The upper portion 80 of the arm 66 is held against movement relative to the upper cuff arm 26 by the upper cuff 42. At this time, the only way to move the arm 66 is at the shoulder 70.

To effect pronation of the hand 68 from the initial orientation of FIGS. 3 and 4 to a palm downward orientation shown in FIGS. 5 and 6, the knob 60 of the main drive assembly 34 is rotated in a counterclockwise direction (as viewed in FIG. 3). Counterclockwise rotation of the knob 60 causes the drive gear 56 (FIG. 9) to rotate the main gear 48 about the axis 36 from the initial position shown in FIGS. 3 and 4 toward the position shown in FIGS. 5 and 6. As this occurs, the sections 118 and 120 (FIG. 1) of the lower cuff 32 firmly grip the distal end portions 90 and 94 (FIG. 2) of the radius and ulna 84 and 86. Therefore, the distal end portions 90 and 94 of the radius and ulna 84 and 86 are rotated with the lower cuff 32 about the axis 36.

As the lower cuff 32 is rotated about the axis 36 from the position shown in FIGS. 3 and 4 toward the position shown in FIGS. 5 and 6, the proximal end portions 92 and 96 of the radius and ulna 84 and 86 move relative to the distal end portion 102 of the humerus. The radius 84 will revolve partially about the ulna 86. The proximal end portion 96 of the ulna will articulate with the distal end portion 102 of the humerus 100. The rotational motion imparted by the lower cuff 32 to the distal end portions 90 and 94 of the radius and ulna 84 and 86 will be isolated to the region between the elbow 78 and wrist 74 in the arm 66 of the patient.

As the drive gear 56 is rotated, the main gear 48 and the lower cuff 32 are rotated together in a clockwise direction (as viewed in FIG. 9) about the axis 36. As this occurs, the extent of pronation of the hand 68 is increased. Rotation of the drive gear 56 and the main gear 48 may be interrupted after the cuff 32 has moved partway from the initial position shown in FIGS. 3 and 4 toward the palm downward orientation shown in FIGS. 5 and 6. Upon interruption of the rotation of the main gear 48 and drive gear 56, the drive gear is effective to hold the main gear against rotation.

This results in stretched viscoelastic material connected with the proximal end portions 92 and 96 of the radius and ulna 84 and 86 being held in a stretched condition. After a short time the viscoelastic material begins to relax. The knob 60 can then be further rotated in a counterclockwise direction (FIGS. 3 and 5) to further stretch the viscoelastic material interconnecting the proximal end portions 92 and 96 of the radius and ulna 84 and 86 and the humerus 100.

Reversing the direction of rotation of the knob 60 rotates the drive gear 56 and main gear 48 to move the lower cuff 32 back to the initial position shown in FIGS. 3 and 4. By rotating the knob 60 in a clockwise direction (as viewed in FIG. 3), the lower cuff 32 and main gear 48 are rotated from the positions shown in FIGS. 5 and 6 back to the initial positions shown in FIGS. 3 and 4. As this occurs, the extent of pronation of the hand 68 is decreased.

The main drive assembly 34 can be operated to increase the extent of supination of the hand 68 from the initial orientation of FIGS. 3 and 4. To accomplish this, the knob 60 is rotated in a clockwise direction (as viewed in FIG. 3). This results in the drive gear or worm 56 rotating the main gear 48 in a counterclockwise direction (as viewed in FIG. 9). As the lower cuff 32 and main gear are rotated in a counterclockwise direction (as viewed in FIG. 9), the extent of supination of the hand 68 is increased as the hand is moved from the position shown in FIGS. 3 and 4 toward the position shown in FIGS. 7 and 8.

As the hand 68 is rotated from the position shown in FIGS. 3 and 4 toward the position shown in FIGS. 7 and 8, the sidewalls 110 and 112 of the lower cuff 32 firmly grip the distal end portions 90 and 94 of the radius and ulna bones 84 and 86. This results in the radius and ulna bones being moved relative to the humerus 100 at the elbow 78. The direction of rotation of the knob 60 can then be reversed to move the hand 68 back toward the initial position of FIGS. 3 and 4.

Although it is preferred to use the orthosis 20 to effect supination and/or pronation of the hand 68, it is contemplated that the orthosis could be modified to be used with other portions of a patient's body if desired. For example, the orthosis 20 could be constructed in such a manner as to effect pronation and/or supination of a foot of a patient.

Orthosis—Second Embodiment

In the embodiment of the orthosis 20 illustrated in FIGS. 1–10, the orthosis is used to effect supination and/or pronation of the hand 68 without changing the extent of bending of the elbow 78. In the embodiment of the invention illustrated in FIG. 11, the orthosis is constructed in such a manner as to effect supination and/or pronation of the hand and to effect bending of the elbow in either flexion or extension. Since the embodiment of the invention illustrated in FIG. 11 is generally similar to the embodiment of the invention illustrated in FIGS. 1–10, similar numerals will be utilized identify similar components, the suffix "a" being associated with the numerals identifying components of FIG. 11 in order to avoid confusion.

An orthosis 20a includes a base 22a. The base 22a has a lower cuff arm 24a and an upper cuff arm 26a. A lower cuff 32a is connected with the lower cuff arm 24a by a main drive assembly 34a. An upper cuff 42a fixedly connected with the upper cuff arm 26a. When an arm 66a of a patient is positioned in the lower and upper cuffs 32a and 42a in the manner previously explained in conjunction with the embodiment of the invention illustrated in FIGS. 1–10, the main drive assembly 34a can be operated to rotate the lower cuff 32a about an axis 36a which extends through a wrist 74a and elbow of the arm 66a.

In accordance with a feature of this embodiment of the invention, a secondary drive assembly 300 is provided to effect relative movement between the lower and upper cuff arms 24a and 26a to bend the arm 66a of the patient at the elbow 78a. The secondary drive assembly 300 includes a main drive gear 302 which is rotatably supported on a shaft 304 which extends through end portions of the lower cuff arm 24a and upper cuff arm 26a. A rack gear 308 is disposed in meshing engagement with the drive gear 302.

Upon rotation of a suitable knob, (not shown) connected with the drive gear 302 through the shaft 304, the drive gear is effective to move the rack 308. Movement of the rack 308 moves the upper cuff arm 26a relative to the lower cuff arm 24a. When the upper cuff arm 26a has been moved to a desired position relative to a lower cuff arm 24a, a latch assembly 312 is operated from a disengaged condition to an engaged condition. When the latch assembly 312 is in the disengaged condition, it is spaced from the drive gear 302 and is connected to the lower cuff arm 24a. When the latch assembly 312 is in the engaged condition it interconnects the cuff arm 24a and drive gear 302. Thus, when the latch assembly 312 is in the engaged condition it engages the teeth on the drive gear 302 to hold the drive gear against rotation relative to the lower cuff arm 24a.

By rotating the main drive gear 302 in a clockwise direction (as viewed in FIG. 11) with the latch assembly 312 disengaged, the rack 308 is moved to effect clockwise (as viewed in FIG. 11) pivotal movement of the upper cuff arm 26a relative to the lower cuff arm 24a. Force is transmitted from the lower cuff 32a to the distal ends 90 and 94 (FIG. 2) of the radius and ulna bones 84 and 86 in the lower portion 76a (FIG. 11) to the arm 66a of the patient. Force is transmitted from the upper cuff 42a to the upper portion 80a of the arm of the patient. As this occurs, the elbow 78a is bent in extension. When the elbow 78a has been bent in extension to the desired extent, the latch assembly 312 is operated from the disengaged condition to the engaged condition to hold the upper cuff arm 26a against movement relative to the lower cuff arm 24a.

Similarly, when the arm 66a is to be bent in flexion, the knob (not shown) connected with the main drive gear 302 is rotated to effect rotation of the main drive gear in a counterclockwise direction (as viewed in FIG. 11). As this occurs, the upper cuff arm 26a is rotated in a counterclockwise direction relative to the lower cuff arm 24a. Of course, at this time, the latch assembly 312 is in the disengaged condition. When the elbow 78 has been bent in flexion to the desired extent, the latch assembly 312 is operated to the engaged condition to hold the gear 302 against rotation relative to the lower and upper cuff arms 24a and 26a.

Orthosis—Third Embodiment

In the embodiment of the orthosis illustrated in FIG. 11, a rack and pinion type drive assembly 300 is provided to effect bending of the arm 66a at the elbow 78a. In the embodiment of the invention illustrated in FIG. 12, a screw and nut type drive assembly is utilized to effect bending the arm at the elbow. Since the embodiment of the invention illustrated in FIG. 12 is generally similar to the embodiments of the invention illustrated in FIGS. 1–11, similar numerals will be utilized to identify similar components, the suffix letter "b" being associated with the components of FIG. 12 in order to avoid confusion.

An orthosis 20b includes a lower cuff arm 24b and an upper cuff arm 26b. A lower cuff 32b is connected with the lower cuff arm 24b by a drive assembly 34b. An upper cuff 42b is connected with the upper cuff arm 26b. Upon operation of the main drive assembly 34b, the lower cuff 32b is rotated about an axis 36b to effect pronation or supination of a hand 68b connected with an arm 66b of a patient, in the manner explained in conjunction with the embodiment of the invention illustrated in FIGS. 1–10.

Figure 12:
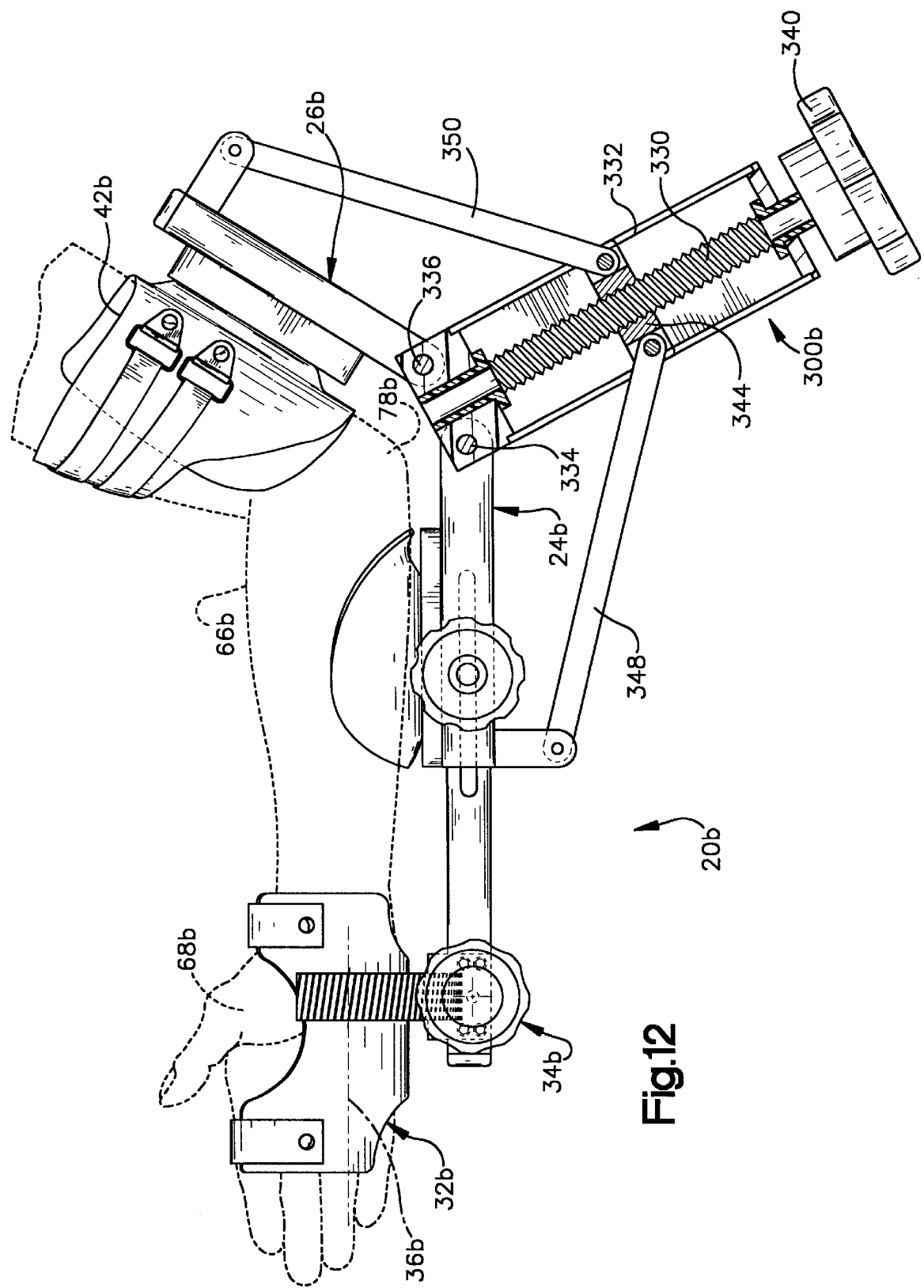
FIG. 12 is a side elevational view, generally similar to FIG. 3, of a third embodiment of the orthosis.

In the embodiment of the invention illustrated in FIG. 12, a secondary drive assembly 300b is connected with the lower cuff arm 24b and upper cuff arm 26b to effect bending of an elbow 78b. The secondary drive assembly 300b includes an externally threaded member or screw 330 which is rotatably supported within a housing 332. A central axis of the screw 330 extends through the elbow 78b. The central axis of the screw 330 extends midway between pivot connections 334 and 336 between the lower cuff arm 24b and upper cuff arm 26b and the housing 332 for the secondary drive assembly 300b.

A manually rotatable knob 340 is connected with the lower end (as viewed in FIG. 12) of the screw 330. An actuator member or block 344 has internal thread convolutions which engage external thread convolutions on the screw 330.

Upon rotation of the input member or knob 340, the actuator member 344 is moved away from the pivot connections 334 and 336. As this occurs, drive links 348 and 350 pivot the lower cuff arm 24b and upper cuff arm 26b about the pivot connections 334 and 336. This effects bending of the elbow 78b in extension. Thus, force is transmitted from the lower cuff 32b to distal ends of the radius and ulna bones in the arm 66b of the patient. Force is transmitted from the upper cuff 42b to the upper portion of the arm of the patient. When the knob 340 is rotated to move the actuator member block 344 toward the pivot connections 334 and 336, the drive links 348 and 350 effect movement of the lower cuff arm 24b and upper cuff arm 26b to bend the elbow 78b in flexion.

Although it is contemplated that the drive assembly 300b could have many different constructions, in the illustrated embodiment of the invention, the drive assembly 300b has the same construction as is disclosed in U.S. Pat. No. 5,503,619 issued Apr. 2, 1996 to Peter M. Bonutti and entitled, "Orthosis for Bending Wrist". The manner in which the arm 66b is bent in flexion or extension is the same as is disclosed in U.S. Pat. No. 5,453,075 issued Sep. 26, 1994 to Peter M. Bonutti and entitled "Orthosis With Distraction Through Range of Motion".

Conclusion

In view of the foregoing description, it is apparent that the present invention provides a new and improved apparatus and method for use in effecting relative movement between bones in an arm 66 or other portion of a body of a patient. The apparatus includes an orthosis 20 having a lower cuff 32 which is rotatable relative to a base 22 by a drive assembly 34 and an upper cuff 42 which is connected to the base. The lower cuff 32 grips a wrist 74 of the patient while the upper cuff 42 grips the upper portion 80 of an arm 66 of the patient. The drive assembly 34 rotates the lower cuff 32 about an axis 36 which extends along the lower portion 76 of the arm 66.

The drive assembly 34 for rotating the lower cuff 32 includes a main gear 48 which is connected with the lower cuff. The lower cuff may extend through an opening 52 in the main gear 48. A drive gear connected with the base 22 is disposed in engagement with the main gear and is rotatable relative to the base to rotate the main gear and lower cuff 32.

A second drive assembly 300 or 300b may be provided to move sections 24a, 26a or 24b, 26b of the base relative to each other and effect bending of the elbow 78a or 78b in the arm of the patient. The second drive assembly 300 or 300b is operable to pivot the sections of the base about an axis which extends transversely to the axis 36a or 36b about which the lower cuff is rotated. Although it is believed that the apparatus and method of the invention will be particularly advantageous when used in association with an arm 66 of a patient, they may be used in association with other portions of a patient's body.

Having described the invention, the following is claimed:

1. An apparatus for use in effecting relative movement between bones in an arm of a patient, said apparatus comprising a base, first cuff means for gripping a wrist portion of the arm of the patient, second cuff means for gripping an upper portion of the arm of the patient, said second cuff means being connected with said base, and drive means connected with said base and said first cuff means for rotating said first cuff means relative to said base about an axis which extends along a lower portion of the arm of the patient, said drive means includes a gear having gear teeth disposed in an arcuate array which forms only a portion of a circle and has spaced apart end portions, said gear having an opening which extends through a peripheral portion of said gear and between the spaced apart end portions of said arcuate array of gear teeth, said first cuff means is connected with said gear to rotate with said gear relative to said base, said first cuff means having an entry portion which is aligned with the opening through the peripheral portion of said gear, said entry portion of said first cuff means is unobstructed along a path extending through the opening in the peripheral portion of said gear to enable a portion of the arm of the patient to move into said first cuff means along the path extending through the opening in the peripheral portion of the gear.

2. An apparatus as set forth in claim 1 wherein said first cuff means grips distal end portions of ulna and radius bones in the arm of the patient, said gear is rotatably mounted to said base to rotate said first cuff means and the distal end portions of the ulna and radius bones in the arm of the patient together about an axis which extends along the lower portion of the arm of the patient.

3. An apparatus as set forth in claim 1 wherein said first cuff means is at least partially disposed in the opening in said gear, said first cuff means having a first end portion which extends in a first direction from said gear, a second end portion which extends in a second direction from said gear, and an intermediate portion which is disposed between said first and second end portions of said first cuff means, said intermediate portion of said first cuff means is at least partially enclosed by said gear and said arcuate array of gear teeth.

4. An apparatus as set forth in claim 1 further including third cuff means connected with said base for engaging the lower portion of the arm of the patient at a location between the wrist and elbow of the arm of the patient, said third cuff means is ineffective to retard rotation of the lower portion of the arm of the patient upon rotation of said first cuff means about the axis which extends along the lower portion of the arm of the patient.

5. An apparatus as set forth in claim 1 wherein said base includes a lower cuff arm which is connected with said drive means and said first cuff means, an upper cuff arm which is connected with said second cuff means, and a pivot connection which extends through and interconnects end portions of said lower and upper cuff arms, said lower cuff arm having a longitudinal axis which extends generally parallel to the axis about which said first cuff means is rotated by said drive means, said upper cuff arm having a longitudinal axis which intersects the longitudinal axis of said lower cuff arm at said pivot connection.

6. An apparatus as set forth in claim 5 wherein said lower cuff arm includes a first section which is connected with said drive means and said first cuff means and a second section which is connected with said pivot connection, said first and second sections of said lower cuff arm is disposed in a telescopic relationship, said first and second sections of said lower cuff arm are extendable to decrease the telescopic relationship between said first and second sections of said lower cuff arm and to move said drive means and said first cuff means away from said pivot connection, said first and second sections of said lower cuff arm are retractable to increase the telescopic relationship between said first and second sections of said lower cuff arm and to move said drive means and said first cuff means toward said pivot connection.

7. An apparatus as set forth in claim 6 further including third cuff means connected with one of said sections of said lower cuff arm for engaging the lower portion of the arm of the patient at a location between the wrist and elbow of the arm of the patient, said third cuff means is connected with said one of said sections of said lower cuff arm for movement therewith relative to the other one of said sections of said lower cuff arm upon a change in the telescopic relationship between said first and second sections of said lower cuff arm.

8. An apparatus as set forth in claim 1 wherein said drive means includes a worm gear which is rotatably connected with said base and is disposed in meshing engagement with said arcuate array of gear teeth, said worm gear is rotatable relative to said base to rotate said arcuate array of gear teeth relative to said base about the axis which extends along the lower portion of the arm of the patient.

9. An apparatus as set forth in claim 1 further including means for connecting said arcuate array of gear teeth with said base and for enabling said arcuate array of gear teeth to rotate relative to said base about the axis which extends along the lower portion of the arm of the patient, said means for connecting said arcuate array of gear teeth with said base and for enabling said arcuate array of gear teeth to rotate relative to said base includes means for engaging said gear at a location radially inward from said arcuate array of gear teeth.

10. An apparatus as set forth in claim 1 wherein said gear includes an arcuate guide surface having a center of curvature disposed on the axis which extends along the lower portion of the arm of the patient, said apparatus further includes a retainer which is connected with said base and engages said arcuate guide surface, said retainer and guide surface cooperate to enable said gear to rotate about the axis which extends along the lower portion of the arm of the patient while retaining said gear against movement in a direction transverse to the axis which extends along the lower portion of the arm of the patient.

11. An apparatus as set forth in claim 1 wherein said first cuff means extends through the opening in the peripheral portion of said gear.

12. An apparatus as set forth in claim 1 wherein said entry portion of said first cuff means is offset from said gear in a direction perpendicular to the axis which extends along the lower portion of the arm of the patient.

13. An apparatus as set forth in claim 1 wherein said first cuff means includes a first section which overlies an inner side of the wrist portion of the arm of the patient and extends through the opening through the peripheral portion of said gear, a second section which overlies an outer side of the wrist portion of the arm of the patient and extends through the opening through the peripheral portion of said gear, and force transmitting means for urging said first and second sections of said first cuff means toward each other to firmly grip the wrist portion of the arm of the patient between said first and second sections of said first cuff means.

14. An apparatus as set forth in claim 1 wherein said base includes a first cuff arm connected with said first cuff means at a location disposed between opposite end portions of said first cuff means, a second cuff arm connected with said second cuff means, and means for pivotally interconnecting said first and second cuff arms and for retaining said first and second cuff arms against relative movement during rotation of said first cuff means by said drive means.

15. An apparatus as set forth in claim 1 wherein said base includes a first cuff arm connected with said first cuff means, a second cuff arm connected with said second cuff means, and means for interconnecting end portions of said first and second cuff arms, said means for interconnecting end portions of said first and second cuff arms includes connector means for pivotally interconnecting said first and second cuff arms for pivotal movement about an axis which extends transverse to the axis about which said drive means rotates said first cuff means and which extends through said end portions of said first and second cuff arms.

16. An apparatus as set forth in claim 1 further including means for rotatably connecting said gear with said base, said means for rotatably connecting said gear with said base includes an arcuate track having a center of curvature disposed on the axis which extends along the lower portion of the arm of the patient, said arcuate track being connected with a first one of said gear and said base, and a follower connected with a second one of said gear and said base and engaging said arcuate track to guide relative movement between said gear and said base.

17. An apparatus as set forth in claim 1 further including a worm disposed in meshing engagement with said arcuate array of gear teeth and connected with said base, said worm is rotatable relative to said base to rotate said gear and said first cuff means relative to said base.

18. An apparatus for use in effecting relative movement between bones in an arm of a patient, said apparatus comprising a base, a first cuff which grips a wrist portion of the arm of the patient, a main gear which is connected with said base, said first cuff extends through said main gear and has a first end portion disposed on a first side of said main gear and a second end portion disposed on a second side of said main gear, said main gear is connected with said first cuff at a location between said first and second end portions of said first cuff, said main gear and first cuff are rotatable together relative to said base, and a second cuff which is connected with said base and which grips an upper portion of the arm of the patient to hold the upper portion of the arm of the patient during rotation of said first cuff and main gear relative to said base.

19. An apparatus as set forth in claim 18 wherein said first cuff includes a first section which extends through said main gear and engages an inner side of the wrist portion of the arm of the patient and a second section which extends through said main gear and engages an outer side of the wrist portion of the arm of the patient, said first and second sections of said first cuff are disposed on opposite sides of an axis about which said first cuff and main gear rotate.

20. An apparatus as set forth in claim 18 wherein said base includes an elongated section which extends along the lower portion of the arm of the patient and has a central axis which is offset from and extends parallel to an axis about which said first cuff and gear rotate, said main gear is at least partially enclosed by said elongated section of said base.

21. An apparatus as set forth in claim 18 wherein said base defines an opening through which said main gear extends, said apparatus further including a retainer which is connected with said base and engages a portion of said main gear which extends through the opening in said base.

22. An apparatus as set forth in claim 18 wherein said main gear has an arcuate array of teeth which is engaged by a rotatable drive gear disposed on said base.

23. An apparatus as set forth in claim 18 wherein said base includes a first cuff arm connected with said first cuff, a second cuff arm connected with said first cuff arm and said second cuff, and a drive assembly which is connected with said first and second cuff arms and is operable to move said first and second cuff arms in a first direction relative to each other to bend an elbow in the arm of the patient in flexion and is operable to move said first and second cuff arms in a second direction relative to each other to bend the elbow in the arm of the patient in extension.

24. An apparatus as set forth in claim 18 wherein said main gear includes surface means for defining an opening through which said first cuff extends, said opening defined by said surface means extends through a peripheral portion of said main gear, said first cuff having an entry portion which is aligned with the opening through the peripheral portion of said main gear, said entry portion of said first cuff being unobstructed along a path extending through the opening in the peripheral portion of said main gear to enable a portion of the arm of the patient to move into said first cuff along the path extending through the opening in the peripheral portion of said main gear.

25. An apparatus as set forth in claim 18 wherein said main gear includes an arcuate array of gear teeth which at least partially enclose said first cuff, a second gear rotatably mounted on said base and disposed in meshing engagement with said main gear, said main gear being rotatable about an axis which extends along a lower portion of the arm of the patient, said second gear is rotatable about an axis which extends transverse to the axis which extends along the arm of the patient.

26. An apparatus as set forth in claim 25 wherein at least a portion of said second gear is enclosed by said base.

27. An apparatus as set forth in claim 18 further including a third cuff connected with said base for engaging the lower portion of the arm of the patient at a location between the wrist and elbow of the arm of the patient, said third cuff being ineffective to retard rotation of the lower portion of the arm of the patient upon rotation of said main gear and first cuff together relative to said base.

28. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said drive means includes a main gear which is connected with said first cuff means and is rotatable with said first cuff means relative to said base and a second gear which is disposed in meshing engagement with said main gear, said second gear is at least partially disposed in a recess in said base.

29. An apparatus as set forth in claim 28 wherein said main gear is rotatable with said first cuff means about the axis which extends along the lower portion of the arm of the patient, said second gear is rotatable about an axis which extends transversely to the axis which extends along the lower portion of the arm of the patient.

30. An apparatus as set forth in claim 28 wherein said first cuff means has first and second end portions and an intermediate portion disposed between said first and second end portions of said first cuff means, said main gear connected with said intermediate portion of said first cuff means at a location between said first and second end portions of said first cuff means.

31. An apparatus as set forth in claim 28 wherein said base includes longitudinally extending upper and lower cuff arms, said lower cuff arm having a first end portion and a second end portion, said second gear is at least partially disposed in a recess formed in said first end portion of said lower cuff arm, said second end portion of said lower cuff arm is pivotally connected to a first end portion of said upper cuff arm, said second cuff means is mounted on said upper cuff arm.

32. An apparatus as set forth in claim 31 wherein said base includes a retainer mounted on said first end portion of said lower cuff arm, said retainer engages opposite sides of said main gear to position said main gear relative to said second gear.

33. An apparatus as set forth in claim 28 wherein said main gear includes an arcuate array of teeth which extends into and out of said recess in said base to engage said second gear.

34. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said first cuff means having first and second end portions which are disposed at spaced apart locations along the axis which extends along the lower portion of the arm of the patient, said drive means includes a main gear which is connected to said first cuff means at a location between said first and second end portions of said first cuff means and a second gear which is rotatably mounted on said base and is disposed in meshing engagement with said main gear.

35. An apparatus as set forth in claim 34 wherein said main gear at least partially encloses a portion of said first cuff means disposed between said first and second end portions of said first cuff means.

36. An apparatus as set forth in claim 34 wherein said base includes a retainer which engages opposite sides of said main gear to position said main gear relative to said base.

37. An apparatus as set forth in claim 34 wherein said second gear is a worm which is mounted on said base and is rotatable relative to said base about an axis which extends transverse to the axis which extends along the lower portion of the patient's arm, said worm is rotatable relative to said base to rotate said first cuff means and said main gear relative to said base.

38. An apparatus as set forth in claim 34 wherein said base includes longitudinally extending arms, and lower cuff arms, said lower cuff arm having a first end portion and a second end portion, said main gear is at least partially disposed between said first end portion of said lower cuff arm and said first cuff means, said second end portion of said lower cuff arm is pivotally connected to a first end portion of said upper cuff arm, said second cuff means is mounted on said upper cuff arm.

39. An apparatus as set forth in claim 38 wherein said first end portion of said first cuff means extends outward of said first end portion of said first cuff arm in a direction away from said second end portion of said first cuff arm.

40. An apparatus as set forth in claim 38 wherein said lower cuff arm includes a first section which is connected with said drive means and a second section which is connected with said pivot connection, said first and second sections of said lower cuff arm are disposed in a telescopic relationship, said first and second sections of said lower cuff arm are extendable to decrease the telescopic relationship between said first and second sections of said lower cuff arm and to move said drive means and said first cuff means away from said pivot connection, said first and second sections of said lower cuff arm are retractable to increase the telescopic relationship between said first and second sections of said lower cuff arm and to move said drive means and said first cuff means toward said pivot connection.

41. An apparatus as set forth in claim 34 wherein said main gear includes an arcuate array of gear teeth which extend at least part way around said first cuff means at said location between said first and second end portions of said first cuff means.

42. An apparatus as set forth in claim 34 wherein said main gear includes surface means which defines an opening which extends axially through said main gear, said first cuff means extends through said opening in said main gear.

43. An apparatus as set forth in claim 34 wherein said main gear has an opening which extends through a peripheral portion of said main gear to a central portion of said main gear, said first cuff means is partially disposed in said opening in said main gear and has an entry portion which is aligned with the opening through the peripheral portion of said main gear, said entry portion of said first cuff means is unobstructed along a path extending through the opening in the peripheral portion of said main gear to enable a portion of the arm of the patient to move into said first cuff means along the path extending through the opening in the peripheral portion of said main gear.

44. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said base includes a lower cuff arm which is connected with said drive means and said first cuff means, an upper cuff arm which is connected with said second cuff means, and a pivot connection which extends through and interconnects end portions of said lower and upper cuff arms, said lower cuff arm having a longitudinal axis which extends generally parallel to an axis about which said first cuff means is rotated by said drive means, said upper cuff arm having a longitudinal axis which intersects the longitudinal axis of said lower cuff arm at said pivot connection.

45. An apparatus as set forth in claim 44 wherein said first cuff means grips distal end portions of ulna and radius bones in the arm of the patient, said drive means includes a gear which is rotatable relative to said base to rotate said first cuff means and the distal end portions of the ulna and radius bones in the arm of the patient together about the axis which extends along the lower portion of the arm of the patient.

46. An apparatus as set forth in claim 44 wherein said drive means includes a gear, said first cuff means is at least partially disposed in an opening in said gear, said first cuff means having a first end portion which extends in a first direction from said gear, a second end portion which extends in a second direction from said gear, and an intermediate portion which is disposed between said first and second end portions of said first cuff means, said intermediate portion of said first cuff means is at least partially enclosed by said gear.

47. An apparatus as set forth in claim 44 further including third cuff means connected with said lower cuff arm of said base for engaging the lower portion of the arm of the patient at a location between the wrist and elbow of the arm of the patient, said third cuff means is ineffective to retard rotation of the lower portion of the arm of the patient upon rotation of said first cuff means about the axis which extends along the lower portion of the arm of the patient.

48. An apparatus as set forth in claim 44 wherein said drive means includes a main gear and a worm which is connected with said base and is disposed in meshing engagement with said main gear, said main gear is connected with said first cuff means, said worm is rotatable relative to said base to rotate said main gear relative to said base about the axis which extends along the lower portion of the arm of the patient.

49. An apparatus as set forth in claim 44 wherein said drive means includes a main gear and means for connecting said main gear with lower cuff arm of said base and for enabling said main gear to rotate relative to said lower cuff arm about the axis which extends along the lower portion of the arm of the patient, said means for connecting said main gear with said base and for enabling said main gear to rotate relative to said base includes means for engaging opposite sides of said main gear at locations radially inward from a peripheral edge portion of said main gear.

50. An apparatus as set forth in claim 44 wherein said drive means includes a main gear having an arcuate guide surface with a center of curvature disposed on the axis which extends along the lower portion of the arm of the patient, said apparatus further includes a retainer which is connected with said lower cuff arm of said base and engages said arcuate guide surface, said retainer and guide surface cooperate to enable said main gear to rotate about the axis which extends along the lower portion of the arm of the patient while retaining said main gear against movement in a direction transverse to the axis which extends along the lower portion of the arm of the patient.

51. An apparatus as set forth in claim 50 wherein said first cuff means extends through an opening in said main gear.

52. An apparatus as set forth in claim 44 wherein said drive means includes a main gear which is connected with said first cuff means and a worm which is disposed in meshing engagement with said main gear, said worm is mounted on said lower cuff arm and is rotatable about an axis which extends perpendicular to the longitudinal axis of said lower cuff arm.

53. An apparatus as set forth in claim 44 wherein said drive means includes a main gear which is connected with said first cuff means and is rotatably mounted on said lower cuff arm, said main gear is rotatable with said first cuff means relative to said lower cuff arm about the axis which extends along the arm of the patient, said drive means further includes a worm which is disposed in meshing engagement with said main gear and is rotatably mounted on said lower cuff arm, said worm is rotatable about an axis which extends perpendicular to the axis about which said main gear is rotatable.

54. An apparatus as set forth in claim 44 wherein said drive means includes a main gear connected with said first cuff means and rotatably mounted on said lower cuff arm by a first retainer which is connected with said lower cuff arm and engages a first side of said main gear and a second retainer which is connected with said lower cuff arm and engages a second side of said main gear, said first and second retainers is disposed in engagement with said first and second sides of said main gear at locations offset from a central axis of said main gear and disposed adjacent to a peripheral edge portion of said main gear.

55. An apparatus as set forth in claim 54 further including a worm disposed in meshing engagement with said main gear and rotatably mounted on said lower cuff arm by a third retainer which is connected with said lower cuff arm and retains said worm against movement along an axis about which said worm is rotatable.

56. An apparatus for use in rotating a first portion of a patient's body relative to a second portion of the patient's body which is connected with the first portion of the patient's body by a joint, said apparatus comprising a base, a first cuff to grip the first portion of the patient's body, a second cuff to grip the second portion of the patient's body, said second cuff is connected with said base, and gear means connected with said first cuff and said base for rotating said first cuff about an axis which extends through the first portion of the patient's body and through the joint interconnecting the first and second portions of the patient's body, said gear means includes a worm which is rotatably mounted on said base for rotation about an axis which extends transverse to the axis which extends through the first portion of the patient's body, and a main gear disposed in meshing engagement with said worm and connected with said first cuff, said worm is rotatable relative to said base to rotate said main gear and said first cuff relative to said base about the axis which extends through the first portion of the patients body, said base includes a first section which is connected with said gear means and said first cuff, a second section which is connected with said second cuff, and connector means which interconnects said first and second sections of said base and enables relative movement to occur between said first and second sections of said base about an axis which extends transverse to the axis about which said first cuff is rotated by said gear means.

57. An apparatus as set forth in claim 56 further including drive means connected with said first and second sections of said base for moving said first and second sections of said base about an axis extending through said connector means to bend the joint which is connected with the first and second portions of the patient's body.

58. An apparatus as set forth in claim 56 further including means for rotatably connecting said main gear with said base, said means rotatably connecting said main gear with said base includes an arcuate track connected with a first one of said main gear and said base, and a follower connected with a second one of said main gear and said base and engaging said arcuate track to guide relative movement between said main gear and said base.

59. An apparatus as set forth in claim 56 wherein said main gear includes means for at least partially defining an opening extending through said main gear, said first cuff and the axis which extends through the first portion of the patient's body and the joint interconnecting the first and second portions of the patient's body both extend into the opening in said main gear.

60. An apparatus as set forth in claim 56 wherein said main gear has an arcuate array of gear teeth which form a portion of a circle, said arcuate array of gear teeth having spaced apart end portions, said main gear having an opening which extends through a central portion of said main gear and between the spaced apart end portions of said arcuate array of gear teeth, said first cuff extends through the opening in said main gear, said first cuff having an entry portion which is aligned with the spaced apart end portions of said arcuate array of gear teeth and through which the first portion of the patient's body moves into said first cuff.

61. An apparatus as set forth in claim 56 further including a third cuff connected with said base and disposed in engagement with the first portion of the patient's body at a location between the first cuff and the joint, said third cuff is ineffective to retard rotation of the first portion of the patient's body upon rotation of said main gear and said first cuff relative to said base.

62. An apparatus as set forth in claim 56 further including a retainer which is mounted on said base and engages opposite sides of said main gear and positions said main gear relative to said worm.

63. An apparatus as set forth in claim 56 further including drive means connected with said first and second sections of said base for effecting relative movement between said first and second sections of said base to bend the joint which is connected with the first and second portions of the patient's body about an axis which extends transverse to the axis about which said first cuff is rotated by said gear means.

64. An apparatus for use in rotating a first portion of a patient's body relative to a second portion of the patient's body which is connected with the first portion of the patient's body by a joint, said apparatus comprising a base, a first cuff to grip the first portion of the patient's body, a second cuff to grip the second portion of the patient's body, said second cuff is connected with said base, gear means connected with said first cuff and said base for rotating said first cuff about an axis which extends through the first portion of the patient's body and through the joint interconnecting the first and second portions of the patient's body, said gear means includes a worm which is rotatably mounted on said base for rotation about an axis which extends transverse to the axis which extends through the first portion of the patient's body, and a main gear disposed in meshing engagement with said worm and connected with said first cuff, said worm is rotatable relative to said base to rotate said main gear and said first cuff relative to said base about the axis which extends through the first portion of the patients body, a third cuff connected with said base and disposed in engagement with the first portion of the patient's body at a location between the first cuff and the joint, said third cuff is ineffective to retard rotation of the first portion of the patient's body upon rotation of said main gear and said first cuff relative to said base.

65. An apparatus for use in effecting relative movement between bones in an arm of a patient, said apparatus comprising a base, first cuff which grips a wrist portion of the arm of the patient, second cuff which grips an upper portion of the arm of the patient, said second cuff is connected with said base, and drive means connected with said base and said first cuff for rotating said first cuff relative to said base about an axis which extends along a lower portion of the arm of the patient, said drive means includes a main gear and a worm, said first cuff is connected with said main gear, said first cuff has a first end portion which extends in a first direction from said main gear, a second end portion which extends in a second direction from said main gear, and an intermediate portion which is disposed between said first and second end portions of said first cuff, said intermediate portion of said first cuff is at least partially enclosed by said main gear, said worm is rotatably mounted on said base and disposed in meshing engagement with said main gear, a first retainer which is connected with said worm and said base and retains said worm against axial movement relative to said base, and a second retainer which is connected with said base and engages opposite sides of said main gear to position said main gear relative to said worm, said worm is rotatable relative to said base about an axis which extends transverse to the axis which extends along the lower portion of the arm of the patient to rotate said main gear and first cuff relative to said base about the axis which extends along the lower portion of the arm of the patient.

66. An apparatus as set forth in claim 65 wherein said first cuff grips distal end portions of ulna and radius bones in the arm of the patient, said main gear being rotatable relative to said base to rotate said first cuff and the distal end portions of the ulna and radius bones in the wrist portion of the arm of the patient together about the axis which extends along the lower portion of the arm of the patient.

67. An apparatus as set forth in claim 65 further including third cuff connected with said base for engaging the lower portion of the arm of the patient at a location between the wrist and elbow of the arm of the patient.

68. An apparatus as set forth in claim 65 wherein said base includes a lower cuff arm which is connected with said drive means and said first cuff, an upper cuff arm which is connected with said second cuff, and a pivot connection which interconnects end portions of said lower and upper cuff arms, said upper and lower cuff arms being pivotal relative to each other about an axis which extends through said pivot connection in a direction transverse to the axis about which said first cuff is rotated by said drive means.

69. An apparatus as set forth in claim 68 wherein said lower cuff arm includes a first section which is connected with said drive means and said first cuff and a second section which is connected with said pivot connection, said first and second sections of said lower cuff arm are disposed in a telescopic relationship, said first and second sections of said lower cuff arm are extendable to decrease the telescopic relationship between said first and second sections of said lower cuff arm and to move said drive means and said first cuff away from said pivot connection, said first and second sections of said lower cuff arm are retractable to increase the telescopic relationship between said first and second sections of said lower cuff arm and to move said drive means and said first cuff toward said pivot connection.

70. An apparatus as set forth in claim 69 further including third cuff connected with one of said sections of said lower cuff arm for engaging the lower portion of the arm of the patient at a location between the wrist and elbow of the arm of the patient, said third cuff is connected with said one of said sections of said lower cuff arm for movement therewith relative to another section of said lower cuff arm upon a change in the telescopic relationship between said first and second sections of said lower cuff arm.

71. An apparatus for use in effecting relative movement between bones in an arm of a patient, said apparatus comprising a base, first cuff which grips a wrist portion of the arm of the patient, second cuff which grips an upper portion of the arm of the patient, said second cuff is connected with said base, and drive means connected with said base and said first cuff for rotating said first cuff relative to said base about an axis which extends along a lower portion of the arm of the patient, said drive means includes a main gear and a worm, said first cuff is connected with said main gear, said worm is rotatably mounted on said base and disposed in meshing engagement with said main gear, a first retainer which is connected with said worm and said base and retains said worm against axial movement relative to said base, and a second retainer which is connected with said base and engages opposite sides of said main gear to position said main gear relative to said worm, said worm is rotatable relative to said base about an axis which extends transverse to the axis which extends along the lower portion of the arm of the patient to rotate said main gear and first cuff relative to said base about the axis which extends along the lower portion of the arm of the patient, said base includes a lower cuff arm which is connected with said drive means and said first cuff, an upper cuff arm which is connected with said second cuff, and a pivot connection which extends through and interconnects end portions of said lower and upper cuff arms, said lower cuff arm having a longitudinal axis which extends generally parallel to the axis about which said first cuff is rotated by said drive means, said upper cuff arm having a longitudinal axis which intersects the longitudinal axis of said lower cuff arm at said pivot connection.

72. An apparatus as set forth in claim 71 wherein said lower cuff arm includes a first section which is connected with said drive means and said first cuff and a second section which is connected with said pivot connection, said first and second sections of said lower cuff arm are disposed in a telescopic relationship, said first and second sections of said lower cuff arm are extendable to decrease the telescopic relationship between said first and second sections of said lower cuff arm and to move said drive means and said first cuff away from said pivot connection, said first and second sections of said lower cuff arm are retractable to increase the telescopic relationship between said first and second sections of said lower cuff arm and to move said drive means and said first cuff toward said pivot connection.

73. An apparatus as set forth in claim 72 further including third cuff connected with one of said sections of said lower cuff arm for engaging the lower portion of the arm of the patient at a location between the wrist and elbow of the arm of the patient, said third cuff is connected with said one of said sections of said lower cuff arm for movement therewith relative to another section of said lower cuff arm upon a change in the telescopic relationship between said first and second sections of said lower cuff arm.

74. An apparatus for use in effecting relative movement between bones in an arm of a patient, said apparatus comprising a base, first cuff means for gripping a wrist portion of the arm of the patient, second cuff means for gripping an upper portion of the arm of the patient, said second cuff means being connected with said base, third cuff means for supporting a lower portion of the arm of the patient at a location between the wrist and elbow of the arm of the patient without retarding movement of the bones in the lower portion of the arm of the patient, said third cuff means is connected with said base, and drive means connected with said base and said first cuff means for rotating said first cuff means relative to said base about an axis which extends along the lower portion of the arm of the patient to move bones in the lower portion of the arm of the patient relative to the elbow of the arm of the patient, said third cuff means is ineffective to retard movement of bones in the lower portion of the arm of the patient upon operation of said drive means to rotate said first cuff means, said base includes longitudinally extending upper and lower cuff arms, said lower cuff arm having a first end portion and a second end portion, said drive means is mounted on said first end portion of said lower cuff arm, said second end portion of said lower cuff arm is pivotally connected to a first end portion of said upper cuff arm, said third cuff means is mounted on an intermediate portion of said lower cuff arm at a location between said first and second end portions of said lower cuff arm, said second cuff means is mounted on said upper cuff arm.

75. An apparatus as set forth in claim 74 wherein said lower cuff arm includes inner and outer sections which are disposed in a telescopic relationship with each other, said first end portion of said lower cuff arm being disposed on said outer section of said lower cuff arm, said second end portion of said lower cuff arm being disposed on said inner section of said lower cuff arm, said outer section of said lower cuff arm is movable relative to said inner section of said lower cuff arm to vary the telescopic relationship between said inner and outer sections of said lower cuff arm and the distance between said first and second cuff means.

76. An apparatus for use in effecting relative movement between bones in an arm of a patient, said apparatus comprising a base, first cuff means for gripping a wrist portion of the arm of the patient, second cuff means for gripping an upper portion of the arm of the patient, said second cuff means being connected with said base, third cuff means for supporting a lower portion of the arm of the patient at a location between the wrist and elbow of the arm of the patient without retarding movement of the bones in the lower portion of the arm of the patient, said third cuff means is connected with said base, and drive means connected with said base and said first cuff means for rotating said first cuff means relative to said base about an axis which extends along the lower portion of the arm of the patient to move bones in the lower portion of the arm of the patient relative to the elbow of the arm of the patient, said third cuff means is ineffective to retard movement of bones in the lower portion of the arm of the patient upon operation of said drive means to rotate said first cuff means, said base includes surface means for defining a recess, said drive means includes a gear having an arcuate array of teeth which extends into and out of said recess in said base and retainer means for engaging opposite sides of said gear to position said gear in said recess.

77. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said drive means includes a worm having a central axis which extends transverse to the axis which extends along the lower portion of the arm of the patient and a rotatable gear disposed in meshing engagement with said worm and rotatable relative to said base about the axis which extends along the arm of the patient, said base includes a first section which is connected with said drive means and said first cuff means, a second section which is connected with said second cuff means, and connector means which interconnects said first and second sections of said base and enables relative movement to occur between said first and second sections of said base about an axis which extends transverse to the axis about which said first cuff means is rotated by said drive means, and second drive means connected with said first and second sections of said base for effecting relative movement between said first and second sections of said base to bend an elbow in the arm of the patient about an axis which extends transverse to the axis about which extends along the lower portion of the arm of the patient.

78. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, drive means connected with said base and said first cuff means for rotating said first cuff means relative to said base about an axis which extends along the lower portion of the arm of the patient, said drive means includes a worm having a central axis which extends transverse to the axis which extends along the lower portion of the arm of the patient and a rotatable gear disposed in meshing engagement with said worm and rotatable relative to said base about the axis which extends along the arm of the patient, and means for rotatably connecting said gear with said base, said means rotatably connecting said gear with said base includes an arcuate track having a center of curvature disposed on the axis which extends along the lower portion of the arm of the patient, said arcuate track is connected with a first one of said gear and said base, and a follower connected with a second one of said gear and said base and engaging said arcuate track to guide relative movement between said gear and said base.

79. An apparatus as set forth in claim 78 wherein said base includes a first section which is connected with said drive means and said first cuff means, a second section which is connected with said second cuff means, and connector means which interconnects said first and second sections of said base and enables relative movement to occur between said first and second sections of said base about an axis which extends transverse to the axis about which said first cuff means is rotated by said drive means.

80. An apparatus as set forth in claim 79 further including second drive means connected with said first and second sections of said base for effecting relative movement between said first and second sections of said base to bend an elbow in the arm of the patient about an axis which extends transverse to the axis about which extends along the lower portion of the arm of the patient.

81. An apparatus as set forth in claim 79 wherein said gear includes means for at least partially defining an opening extending through said gear, said first cuff means, and the axis which extends along the lower portion of the arm of the patient both extend through the opening in said gear.

82. An apparatus as set forth in claim 78 wherein said gear has an arcuate array of gear teeth which form a portion of a circle, said arcuate array of gear teeth having spaced apart end portions, said gear having an opening which extends through said gear and between the spaced apart end portions of said arcuate array of gear teeth, said first cuff means having an entry portion which is aligned with the spaced apart end portions of said arcuate array of gear teeth and through which the arm of the patient moves into said first cuff.

83. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said drive means includes a worm having a central axis which extends transverse to the axis which extends along the lower portion of the arm of the patient and a rotatable gear disposed in meshing engagement with said worm and rotatable relative to said base about the axis which extends along the arm of the patient, said gear includes means for at least partially defining an opening extending through said gear, said first cuff means and the axis which extends along the lower portion of the arm of the patient both extend through the opening in said gear.

84. An apparatus as set forth in claim 83 wherein said base includes a first section which is connected with said drive means and said first cuff means, a second section which is connected with said second cuff means, and connector means which interconnects said first and second sections of said base and enables relative movement to occur between said first and second sections of said base about an axis which extends transverse to the axis about which said first cuff means is rotated by said drive means.

85. An apparatus as set forth in claim 83 further including second drive means connected with said first and second sections of said base for effecting relative movement between said first and second sections of said base to bend an elbow in the arm of the patient about an axis which extends transverse to the axis about which extends along the lower portion of the arm of the patient.

86. An apparatus as set forth in claim 83 further including means for rotatably connecting said gear with said base, said means rotatably connecting said gear with said base includes an arcuate track having a center of curvature disposed on the axis which extends along the lower portion of the arm of the patient.

87. An apparatus as set forth in claim 83 wherein said gear has an arcuate array of gear teeth which extends around a portion of the opening through said gear, said arcuate array of gear teeth having spaced apart end portions, said first cuff means having an entry portion which is aligned with the spaced apart end portions of said arcuate array of gear teeth and through which the arm of the patient moves into said first cuff means.

88. An apparatus as set forth in claim 83 further including a third cuff connected with said base and disposed in engagement with the lower portion of the arm of the patient at a location between the wrist and elbow of the arm of the patient, said third cuff is ineffective to retard rotation of the lower portion of the arm of the patient upon rotation of said gear and said first cuff means relative to said base.

89. An apparatus as set forth in claim 83 further including a retainer which is mounted on said base and engages opposite sides of said gear and positions said gear relative to said worm.

90. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said drive means includes a worm having a central axis which extends transverse to the axis which extends along the lower portion of the arm of the patient and a rotatable gear disposed in meshing engagement with said worm and rotatable relative to said base about the axis which extends along the arm of the patient, said gear has an arcuate array of gear teeth which form a portion of a circle, said arcuate array of gear teeth having spaced apart end portions, said gear having an opening which extends through said gear and between the spaced apart end portions of said arcuate array of gear teeth, said first cuff means having an entry portion which is aligned with the spaced apart end portions of said arcuate array of gear teeth and through which the arm of the patient moves into said first cuff means.

91. An apparatus as set forth in claim 90 wherein said base includes a first section which is connected with said gear and said first cuff means, a second section which is connected with said second cuff means, and connector means which interconnects said first and second sections of said base.

92. An apparatus as set forth in claim 90 further including second drive means connected with said first and second cuff means for effecting relative movement between said first and second cuff means to bend an elbow in the arm of the patient.

93. An apparatus as set forth in claim 90 further including means for rotatably connecting said gear with said base, said means rotatably connecting said gear with said base includes an arcuate track connected with said gear and having a center of curvature disposed on an axis which extends through a center of curvature of said arcuate array of gear teeth, and a follower connected with said base and engaging said arcuate track to guide relative movement between said gear and said base.

94. An apparatus as set forth in claim 90 wherein said gear and worm are disposed in meshing engagement at a location between a portion of said base and said first cuff means.

95. An apparatus as set forth in claim 90 further including a third cuff connected with said base and disposed in engagement with the lower portion of the arm of the patient at a location between the wrist and elbow of the arm of the patient.

96. An apparatus as set forth in claim 90 further including a retainer which is mounted on said base and engages opposite sides of said gear and positions said gear relative to said worm.

97. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said base includes a lower cuff arm which is connected with said drive means and said first cuff means, an upper cuff arm which is connected with said second cuff means, and a pivot connection which interconnects end portions of said lower and upper cuff arms, said lower cuff arm includes a first section which is connected with said drive means and said first cuff means and a second section which is connected with said pivot connection, said first and second sections of said lower cuff arm are disposed in a telescopic relationship, said first and second sections of said lower cuff arm are extendable to decrease the telescopic relationship between said first and second sections of said lower cuff arm and to move said drive means and said first cuff means away from said pivot connection, said first and second sections of said lower cuff arm are retractable to increase the telescopic relationship between said first and second sections of said lower cuff arm and to move said drive means and said first cuff means toward said pivot connection, said lower cuff arm has a longitudinal axis which extends generally parallel to the axis about which said first cuff means is rotated by said drive means, said upper cuff arm having a longitudinal axis which intersects the longitudinal axis of said lower cuff arm at said pivot connection.

98. An apparatus as set forth in claim 97 wherein said first cuff means grips distal end portions of ulna and radius bones in the arm of the patient, said drive means includes a gear which is rotatable relative to said base to rotate said first cuff means and the distal end portions of the ulna and radius bones in the arm of the patient together about the axis which extends along the lower portion of the arm of the patient.

99. An apparatus as set forth in claim 97 wherein said drive means includes a gear, said first cuff means being at least partially disposed in an opening in said gear.

100. An apparatus as set forth in claim 97 further including third cuff means connected with said lower cuff arm for engaging the lower portion of the arm of the patient at a location between the wrist and elbow of the arm of the patient.

101. An apparatus as set forth in claim 97 further including third cuff means connected with one of said sections of said lower cuff arm for engaging the lower portion of the arm of the patient at a location between the wrist and elbow of the arm of the patient, said third cuff means is connected with said one of said sections of said lower cuff arm for movement therewith relative to the other one of said sections of said lower cuff arm upon a change in the telescopic relationship between said first and second sections of said lower cuff arm.

102. An apparatus as set forth in claim 97 wherein said drive means includes a main gear and a worm which is connected with said first section of said base and is disposed in meshing engagement with said main gear, said main gear is connected with said first cuff means, said worm is rotatable relative to said base to rotate said main gear relative to said base about the axis which extends along a lower portion of the arm of the patient.

103. An apparatus as set forth in claim 97 wherein said drive means includes a main gear and means for connecting said main gear with said first section of said base and for enabling said main gear to rotate relative to said first section of said base about the axis which extends along the lower portion of the arm of the patient.

104. An apparatus as set forth in claim 97 wherein said drive means includes a main gear having an arcuate guide surface, said apparatus further includes a retainer which is connected with said first section of said lower cuff arm and engages said arcuate guide surface, said retainer and guide surface cooperate to enable said main gear to rotate while retaining said main gear against movement in a direction transverse to the lower portion of the arm of the patient.

105. An apparatus as set forth in claim 104 wherein said first cuff means extends into an opening in said main gear.

106. An apparatus as set forth in claim 97 wherein said drive means includes a main gear which is connected with said first cuff means and a worm which is disposed in meshing engagement with said main gear.

107. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said drive means includes a gear, said first cuff means is at least partially disposed in an opening in said gear, said first cuff means having a first end portion which extends in a first direction from said gear, a second end portion which extends in a second direction from said gear, and an intermediate portion which is disposed between said first and second end portions of said first cuff means, said intermediate portion of said first cuff means is at least partially enclosed by said gear, said base includes a lower cuff arm which is connected with said drive means and said first cuff means, an upper cuff arm which is connected with said second cuff means, and a pivot connection which interconnects end portions of said lower and upper cuff arms, said lower cuff arm includes a first section which is connected with said drive means and said first cuff means and a second section which is connected with said pivot connection, said first and second sections of said lower cuff arm are disposed in a telescopic relationship, said first and second sections of said lower cuff arm are extendable to decrease the telescopic relationship between said first and second sections of said lower cuff arm and to move said drive means and said first cuff means away from said pivot connection, said first and second sections of said lower cuff arm are retractable to increase the telescopic relationship between said first and second sections of said lower cuff arm and to move said drive means and said first cuff means toward said pivot connection.

108. An apparatus as set forth in claim 107 wherein said lower cuff arm has a longitudinal axis which extends generally parallel to the axis about which said first cuff means is rotated by said drive means, said upper cuff arm having a longitudinal axis which extends transversely to the longitudinal axis of said lower cuff arm.

109. An apparatus as set forth in claim 107 wherein said first cuff means grips distal end portions of ulna and radius bones in the arm of the patient, said gear is rotatable relative to said base to rotate said first cuff means and the distal end portions of the ulna and radius bones in the arm of the patient together about the axis which extends along the lower portion of the arm of the patient.

110. An apparatus as set forth in claim 107 further including third cuff means connected with said lower cuff arm for engaging the lower portion of the arm of the patient at a location between the wrist and elbow of the arm of the patient.

111. An apparatus as set forth in claim 107 further including third cuff means for engaging the lower portion of the arm of the patient at a location between the wrist and elbow of the arm of the patient, said third cuff means being connected with said lower cuff arm.

112. An apparatus as set forth in claim 107 wherein said drive means includes a worm which is connected with said base and is disposed in meshing engagement with said gear, said worm is rotatable relative to said base to rotate said gear and said first cuff means relative to said base about the axis which extends along a lower portion of the arm of the patient.

113. An apparatus as set forth in claim 107 wherein said drive means includes means for connecting said gear with said first section of said lower cuff arm and for enabling said gear and said first cuff means to rotate relative to said first section of said lower cuff arm about the axis which extends along a lower portion of the arm of the patient.

114. An apparatus as set forth in claim 107 wherein said gear has an arcuate guide surface with a center of curvature disposed on the axis which extends along the lower portion of the arm of the patient, said apparatus further includes a retainer which is connected with said first section of said lower cuff arm and engages said arcuate guide surface.

115. An apparatus as set forth in claim 107 further including second drive means connected with said lower and upper cuff arms for moving said lower and upper cuff arms relative to each other about an axis which extends through said pivot connection.

116. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said base includes a lower cuff arm which is connected with said drive means and said first cuff means, an upper cuff arm which is connected with said second cuff means, and a pivot connection which interconnects end portions of said lower and upper cuff arms, said lower cuff arm includes a first section which is connected with said drive means and said first cuff means and a second section which is connected with said pivot connection, said first and second sections of said lower cuff arm are disposed in a telescopic relationship, said first and second sections of said lower cuff arm are extendable to decrease the telescopic relationship between said first and second sections of said lower cuff arm and to move said drive means and said first cuff means away from said pivot connection, said first and second sections of said lower cuff arm are retractable to increase the telescopic relationship between said first and second sections of said lower cuff arm and to move said drive means and said first cuff means toward said pivot connection, said drive means includes a main gear and means for connecting said main gear with said first section of said lower cuff arm and for enabling said main gear to rotate relative to said first section of said lower cuff arm about the axis which extends along the lower portion of the arm of the patient, said means for connecting said main gear with said base and for enabling said main gear to rotate relative to said base includes means for engaging said main gear at a location radially inward from and adjacent to a peripheral edge of said main gear.

117. An apparatus as set forth in claim 116 wherein said first cuff means grips distal end portions of ulna and radius bones in the arm of the patient, said main gear is connected to said first cuff means to rotate said first cuff means and the distal end portions of the ulna and radius bones in the arm of the patient together about the axis which extends along the lower portion of the arm of the patient.

118. An apparatus as set forth in claim 116 wherein said first cuff means is at least partially disposed in an opening in said main gear and is connected for rotation therewith about the axis which extends along the lower portion of the arm of the patient.

119. An apparatus as set forth in claim 118 further including third cuff means connected with said second section of said lower cuff arm for engaging the lower portion of the arm of the patient at a location between the wrist and elbow of the arm of the patient, said third cuff means is ineffective to retard rotation of the lower portion of the arm of the patient upon rotation of said first cuff means about the axis which extends along the lower portion of the arm of the patient.

120. An apparatus as set forth in claim 116 further including third cuff means connected with one of said sections of said lower cuff arm for engaging the lower portion of the arm of the patient at a location between the wrist and elbow of the arm of the patient, said third cuff means is connected with said one of said sections of said lower cuff arm for movement therewith relative to the other one of said sections of said lower cuff arm upon a change in the telescopic relationship between said first and second sections of said lower cuff arm.

121. An apparatus as set forth in claim 116 wherein said drive means includes a worm which is connected with said first section of said lower cuff arm and is disposed in meshing engagement with said main gear, said main gear is connected with said first cuff means, said worm is rotatable relative to said lower cuff arm to rotate said main gear and said first cuff means together relative to said base about the axis which extends along a lower portion of the arm of the patient.

122. An apparatus as set forth in claim 116 wherein said first cuff means extends through an opening in said main gear.

123. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said base includes a lower cuff arm which is connected with said drive means and said first cuff means, an upper cuff arm which is connected with said second cuff means, and a pivot connection which interconnects end portions of said lower and upper cuff arms, said lower cuff arm includes a first section which is connected with said drive means and said first cuff means and a second section which is connected with said pivot connection, said first and second sections of said lower cuff arm are disposed in a telescopic relationship, said first and second sections of said lower cuff arm are extendable to decrease the telescopic relationship between said first and second sections of said lower cuff arm and to move said drive means and said first cuff means away from said pivot connection, said first and second sections of said lower cuff arm are retractable to increase the telescopic relationship between said first and second sections of said lower cuff arm and to move said drive means and said first cuff means toward said pivot connection, said drive means includes a main gear having an arcuate guide surface with a center of curvature disposed on the axis which extends along the lower portion of the arm of the patient, said apparatus further includes a retainer which is connected with said first section of said base and engages said arcuate guide surface, said retainer and guide surface cooperate to enable said main gear to rotate about the axis which extends along the lower portion of the arm of the patient while retaining said main gear against movement in a direction transverse to the axis which extends along the lower portion of the arm of the patient.

124. An apparatus as set forth in claim 123 wherein said first cuff means extends through an opening in said main gear.

125. An apparatus for use in effecting relative movement between bones in an arm of a patient, said apparatus comprising a base, first cuff means for gripping a wrist portion of the arm of a patient, second cuff means for gripping an upper portion of the arm of the patient, said second cuff means is connected with said base, and drive means connected with said base and said first cuff means for rotating said first cuff means relative to said base about an axis which extends along the lower portion of the arm of the patient, said base includes a lower cuff arm which is connected with said drive means and said first cuff means, an upper cuff arm which is connected with said second cuff means, and a pivot connection which interconnects end portions of said lower and upper cuff arms, said lower cuff arm includes a first section which is connected with said drive means and said first cuff means and a second section which is connected with said pivot connection, said first and second sections of said lower cuff arm are disposed in a telescopic relationship, said first and second sections of said lower cuff arm are extendable to decrease the telescopic relationship between said first and second sections of said lower cuff arm and to move said drive means and said first cuff means away from said pivot connection, said first and second sections of said lower cuff arm are retractable to increase the telescopic relationship between said first and second sections of said lower cuff arm and to move said drive means and said first cuff means toward said pivot connection, said lower and upper cuff arms are pivotal relative to each other at said pivot connection about a pivot axis which extends transverse to the axis which extends along the lower portion of the arm of the patient, said drive means includes a main gear which is connected with said first cuff means and a worm which is disposed in meshing engagement with said main gear, said worm is rotatable about an axis which extends parallel to said pivot axis.

126. An apparatus as set forth in claim 125 further including second drive means connected with said base and operable to effect pivotal movement of said lower and upper cuff arms relative to each other about the pivot axis which extends transverse to the axis which extends along the arm of the patient.

127. An apparatus as set forth in claim 125 wherein said first cuff means extends through said main gear.

128. An apparatus as set forth in claim 125 wherein said worm and main gear are disposed in meshing engagement at a location disposed between said first cuff means and a portion of said first section of said lower cuff arm.

* * * * *

UNITED STATES PATENT AND TRADEMARK OFFICE
CERTIFICATE OF CORRECTION

PATENT NO. : 5,848,979
DATED : December 15, 1998
INVENTOR(S) : Peter M. Bonutti et al.

It is certified that error appears in the above-identified patent and that said Letters Patent is hereby corrected as shown below:

Col. 15, line 31
  replace "is"
  with --are--.
Col. 18, line 29
  replace "gear connected"
  with --gear is connected--.
Col. 21, line 29
  replace "is"
  with --are--.

Signed and Sealed this

Twenty-ninth Day of June, 1999

Attest:

Q. TODD DICKINSON

*Attesting Officer*     *Acting Commissioner of Patents and Trademarks*